United States Patent
Toyoda et al.

(10) Patent No.: US 10,790,051 B2
(45) Date of Patent: Sep. 29, 2020

(54) MEDICAL SUPPORT SYSTEM, INFORMATION TERMINAL APPARATUS, PATIENT IMAGE DATA ACQUISITION METHOD AND PATIENT INFORMATION ACQUISITION METHOD

(71) Applicant: Olympus Corporation, Hachioji (JP)

(72) Inventors: Tetsuya Toyoda, Hachioji (JP); Masaru Ikeda, Fujimi (JP); Hideaki Yoshida, Hachioji (JP); Kazuhiko Osa, Hachioji (JP); Osamu Nonaka, Sagamihara (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 16/297,393

(22) Filed: Mar. 8, 2019

(65) Prior Publication Data
US 2019/0341129 A1 Nov. 7, 2019

(30) Foreign Application Priority Data
May 1, 2018 (JP) ................................. 2018-088336

(51) Int. Cl.
| | | |
|---|---|---|
| G16H 10/60 | (2018.01) | |
| G16H 30/20 | (2018.01) | |
| H04N 5/232 | (2006.01) | |

(52) U.S. Cl.
CPC ............. *G16H 10/60* (2018.01); *G16H 30/20* (2018.01); *H04N 5/23222* (2013.01)

(58) Field of Classification Search
None
See application file for complete search history.

(56) References Cited

U.S. PATENT DOCUMENTS

| | | | | |
|---|---|---|---|---|
| 2015/0180917 A1* | 6/2015 | Im | ....................... | H04N 5/23222 |
| | | | | 348/14.01 |
| 2019/0050540 A1* | 2/2019 | Yoo | ....................... | G16H 10/20 |

FOREIGN PATENT DOCUMENTS

| | | |
|---|---|---|
| JP | 2001-299767 A | 10/2001 |
| JP | 2006-195669 | 7/2006 |
| JP | 2017-049695 A | 3/2017 |
| JP | 2017-216005 A | 12/2017 |

OTHER PUBLICATIONS

Office Action from corresponding Japanese Patent Application Serial No. 2018-088336, dated Jun. 18, 2019 (9 pgs.).

* cited by examiner

*Primary Examiner* — Edemio Navas, Jr.
(74) *Attorney, Agent, or Firm* — John C. Pokotylo; Pokotylo Patent Services

(57) ABSTRACT

A medical support system supporting medical services even at a remote location, by a first information terminal apparatus operated by a doctor that gives medical examination to a patient and a second information terminal apparatus by which a helper can photograph an image of the patient at a location away from the doctor sharing information about the patient, the medical support system including: the first information terminal apparatus configured to transmit information that is information corresponding to request information from the helper and is photographing condition information for the helper to photograph the patient; and the second information terminal apparatus configured to acquire information about the photographing condition information received from the first information terminal apparatus to photograph the patient.

26 Claims, 11 Drawing Sheets

MEDICAL SUPPORT SYSTEM, INFORMATION TERMINAL APPARATUS, PATIENT IMAGE DATA ACQUISITION METHOD AND PATIENT INFORMATION ACQUISITION METHOD

CROSS REFERENCE TO RELATED APPLICATION

This application claims the benefit of Japanese Application No. 2018-088336 filed in Japan on May 1, 2018, the contents of which are incorporated herein by this reference.

BACKGROUND OF THE INVENTION

1. Field of the Invention

The present invention relates to a medical support system for supporting medical services by sharing patient information including image data, an information terminal apparatus applied to the medical support system to handle the image data in the patient information, a patient image data acquisition method for acquiring the patient image data included in the patient information and a patient information acquisition method.

2. Description of the Related Art

Recently, information terminal apparatuses capable of easily handling various kinds of electronic information including image information, which are provided with a communication function and are in a small-sized and portable form, have been generally widespread.

This kind of information terminal apparatus is configured to be capable of directly performing mutual communication with other information terminal apparatuses of a same kind to exchange various kinds of electronic information and capable of accessing a file server or the like at a remote location via a network to perform communication (transmission/reception) of various kinds of electronic information with the file server or the like.

Therefore, conventionally, network systems configured to be capable of handling various kinds of electronic information and performing information sharing by using ICT (information and communication technology) for mutually connecting a plurality of such information terminal apparatuses and a file server in which various kinds of electronic information have been accumulated, via an existing network or a dedicated network have been commonly in practical use and are rapidly spread in various kinds of fields.

As this type of network system, there is, for example, in a medical field, a medical support system (for example, a hospital information system (HIS) or the like) configured so that medical workers and the like (various kinds of qualified medical workers, for example, doctors, nurses, various kinds of professional technicians (such as workers qualified to handle apparatuses) and care workers) can access a file server installed in a medical facility such as a hospital via an external network or an internal network using information terminal apparatuses and perform mutual communication with the file server to share medical-related information (for example, electronic medical record information and patient information).

As for this kind of medical support system, various proposals have been conventionally disclosed by Japanese Patent Application Laid-Open Publication No. 2006-195669 and the like.

Medical support systems disclosed by Japanese Patent Application Laid-Open Publication No. 2006-195669 and the like perform electronic medical record management, order management, business schedule management and the like using information terminal apparatuses used inside and outside a medical facility and provided with various kinds of functions such as a voice communication function, a data communication function and a personal authentication function.

It is thought that this kind of medical support system is used, for example, for medical care services for patients who are difficult to visit a hospital, such as online medical care, visiting medical care and visiting nursing care. In this case, for example, it becomes possible for a patient who is difficult to move himself/herself or a patient who lives at a remote location far from a medical facility such as a hospital, by using the medical support system, easily receive medical care, medical consultation and the like by a doctor without going to a medical facility such as a hospital.

If a medical worker such as a nurse or a care worker who visits a patient, or a caregiver such as the patient's family member or close relative who is in the patient's home can acquire image information and the like as patient information using a predetermined information terminal apparatus, communicate the acquired patient information (the image information and the like) to a file server installed in a medical facility such as a hospital to accumulate the patient information in the file server, and share the patient information (the image information) with a doctor in charge of the patient, then such convenience that the doctor can perform follow-up observation of the patient and grasp the patient's current situation by referring to images without visiting the patient for medical care is conceivable.

In the medical field in recent years, medical image apparatuses in various kinds of forms that treat medical images (for example, X-ray images, CT (computed tomography) images, MRI (magnetic resonance imaging) images, ultrasonic tomographic images, angiographic images, endoscopic images, thermography images, microscopic images and ordinary picture images) as electronic image data have been in practical use and widespread.

Further, network standards (for example, the DICOM (Digital Imaging and Communications in Medicine) standard) for connecting the medical image apparatuses in the various kinds of forms so that image data acquired and handled by the respective apparatuses and accompanying information of the image data can be mutually shared have been in practical use.

In general, it is assumed that a medical image officially recognized as patient information is only image information that is acquired based on specified settings and format by a predetermined medical-related qualified worker (a medical worker) using a predetermined medical image apparatus in response to information including a plurality of instructions from a doctor.

Therefore, an image of an affected part, a symptom or the like acquired by a person without a predetermined medical-related qualification (for example, a caregiver such as a patient's family member or close relative or the patient himself/herself; hereinafter, such a person will be referred to as a non-medical worker) using, for example, an image pickup apparatus in a general form (for example, a digital camera) or a communication terminal apparatus that is generally widespread (for example, a smartphone or a tablet PC) normally cannot be treated as an official medical image.

Recently, however, small-size communication terminal apparatuses provided with an image pickup function capable of easily acquiring a high-resolution image as well as a communication function, which is suitable to carry (more specifically, for example, a smartphone and a tablet PC) have been generally widespread.

Furthermore, among image pickup apparatuses such as digital cameras, image pickup apparatuses provided with a communication function have been in practical use. In description below, such communication-function-equipped pickup apparatuses, image-pickup-function-equipped communication apparatuses and the like will be generically referred to as information terminal apparatuses.

As described above, in recent years, an environment in which anyone can acquire a high-resolution image anytime, and acquired image data can be easily shared with others having similar information communication terminal apparatuses has been established.

Therefore, for example, if not only image data acquired by medical workers but also image data acquired by non-medical workers, for example, using their own information terminal apparatuses in a general form (for example, digital cameras, smartphones and tablet PCs) can be handled as medical reference images as patient information, it will be very convenient.

For this purpose, if it is possible, for example, to convert a file format or the like (a storage format) of image data to a format in conformity with an existing medical network standard (for example, the DICOM standard), it becomes possible to share data with medical workers such as doctors using a corresponding existing medical network. That is, by using a general terminal such as a camera and a smartphone, a non-medical worker can easily obtain reliable image information that a doctor at a remote place can use as an aid to medical care and diagnosis.

SUMMARY OF THE INVENTION

A medical support system of one aspect of the present invention is a medical support system supporting medical services even at a remote location, by a first information terminal apparatus operated by a doctor that gives medical examination to a patient and a second information terminal apparatus by which a helper can photograph an image of the patient at a location away from the doctor sharing information about the patient, the medical support system being provided with: the first information terminal apparatus configured to transmit information that is information corresponding to request information from the helper and is photographing condition information for the helper to photograph the patient; and the second information terminal apparatus configured to acquire information about the photographing condition information received from the first information terminal apparatus to photograph the patient.

An information terminal apparatus of another aspect of the present invention is provided with: a communication device comprising a receiving device configured to receive particular use information including photographing condition information created based on request information from a photographer and information clarifying being used for a medical action; an image pickup device configured to acquire image data; a processor configured to associate the image data acquired by the image pickup device with the particular use information received by the communication device; and a recording device configured to record particular use image data in a form in which the image data and the particular use information are associated by the processor.

A patient image data acquisition method of one aspect of the present invention is a method for acquiring patient image data handled in a medical support system supporting medical services by sharing information about a remote patient, the method including: transmitting particular use information including photographing condition information created in response to request information from a terminal of a person near the remote patient and information clarifying being used for a medical action; and acquiring image data by photographing according to the particular use information, by the information terminal apparatus and recording the acquired image data and the particular use information in association with each other.

A patient information acquisition method of one aspect of the present invention is a patient information acquisition method for acquiring information about a patient, the method including: receiving request information including target patient information and apparatus information usable by a user to create guidance information according to the request information; and acquiring additional information acquired according to the guidance information.

Benefit of the present invention will be further apparent from following detailed description.

DETAILED DESCRIPTION OF THE PREFERRED EMBODIMENTS

Figure 1:
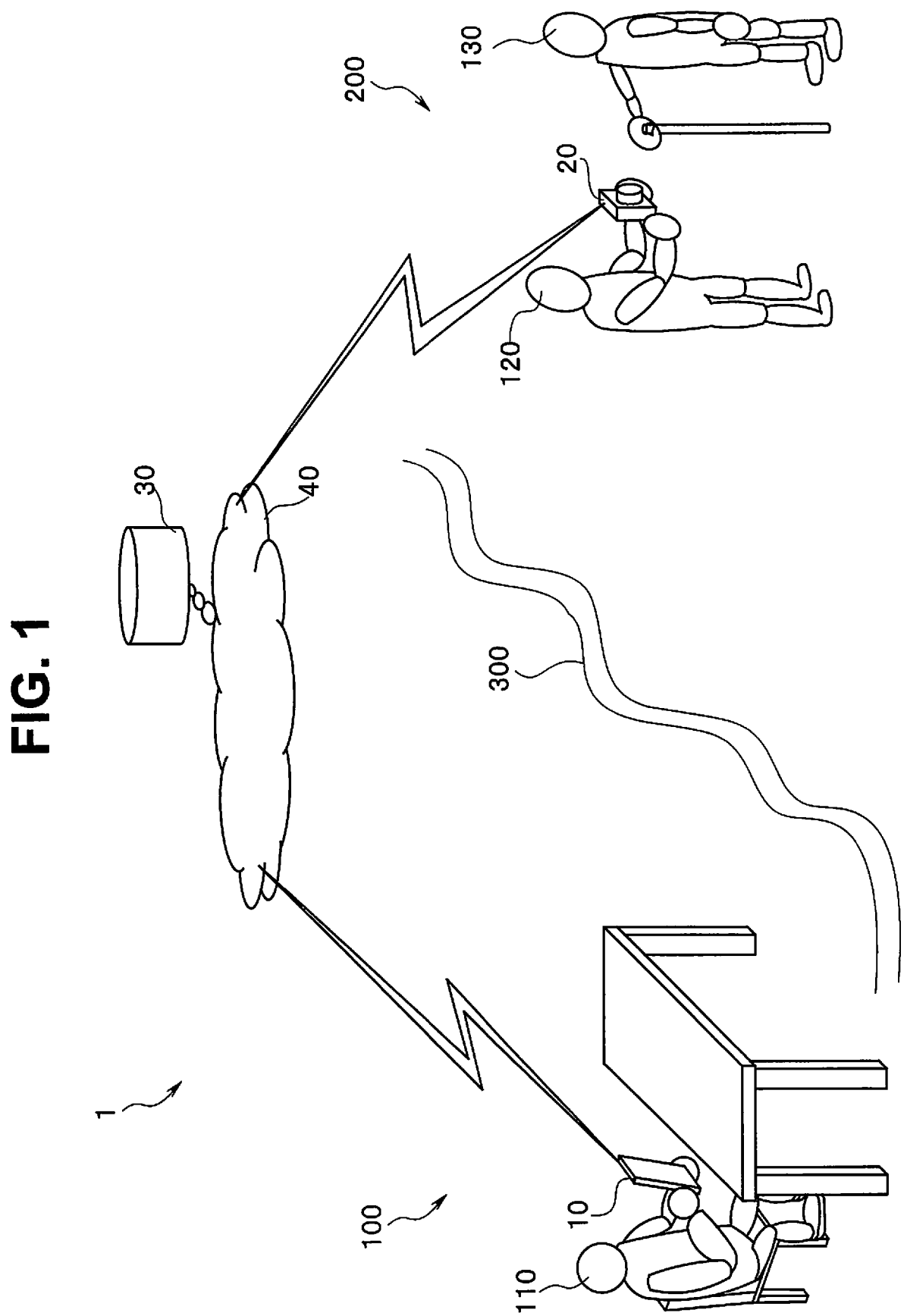
FIG. 1 is a conceptual diagram showing an outline configuration of a medical support system of one embodiment of the present invention.

The present invention will be described below by an embodiment shown by drawings. Each drawing used in the description below is schematic, and a dimensional relationship, reduced scales and the like of respective members may be shown different for each component in order to show the component in a recognizable size on the drawing. Therefore, as for the quantity of each component, the shape of each component, a ratio of sizes among respective components, relative positional relationships among the respective components and the like described in each of the drawings, the present invention is not limited to a form shown in the drawing.

One Embodiment

A medical support system of one embodiment of the present invention is an example of a network system for realizing data sharing of medical-related information, for example, using an existing network used in a medical facility such as a hospital and an image acquisition apparatus in a normal form that is generally widespread (for example, an image pickup apparatus such as a digital camera and an information terminal apparatus such as a smartphone) to support medical services.

More specifically, the medical support system of the present embodiment is a network system that realizes sharing of data of medical-related information such as patient information including images as information to be supplied for a particular purpose (for a medical use) acquired using "general image apparatuses" (*2), that is, image data of "medical images", "medical reference images" (*4) and the like, in addition to a function realized in a conventional network system (a function of sharing data of medical-related information such as patient information including image data like "medical images" (*3) acquired using "medical image apparatuses" (*1), to support medical services.

(*1 "Medical Image Apparatuses")

Here, the "medical image apparatuses" are image acquisition apparatuses configured to be specifically used at sites in a particular field (here, the medical field). For example, apparatuses such as X-ray photographing apparatus (including CT imaging apparatuses and angiography apparatuses), MRI apparatuses, ultrasonic tomography apparatuses, endoscope apparatuses, thermography apparatuses and microscopic photographing apparatuses correspond to the medical image apparatuses.

The medical image apparatuses are installed mainly in medical field facilities (for example, hospitals) and intended to be used only by medical-related qualified workers (referring to so-called medical staff such as doctors, nurses and various kinds of professional technicians; hereinafter referred to as medical workers) to acquire "medical images" (to be described later).

The medical image apparatuses are not assumed to be used by persons other than medical workers including doctors. Therefore, all of images acquired by the medical image apparatuses are approved as "medical images" (to be described later).

(*2 "General Image Apparatuses")

The "general image apparatuses" are image acquisition apparatuses other than conventional "medical image apparatuses" and are assumed to be image acquisition apparatuses in a normal form that are generally widespread (for example, image pickup apparatuses such as digital cameras and image-pickup-function-equipped information terminal apparatuses such as smartphones).

In this case, the "general image apparatuses" assume that:

(1) a case of being permanently provided in medical facilities and used by medical workers belonging to the medical facilities; and (2) a case of being owned by persons other than medical workers (for example, caregivers such as patients' family members and relatives, or the patients themselves; hereinafter, such persons will be referred to as non-medical workers) and used by the non-medical workers such as the owners and the relatives.

Therefore, images acquired by the "general image apparatuses" include "medical images" (to be described later) and "medical reference images" (to be described later).

(*3 "Medical Images)

The "medical images" are image information acquired by medical workers including doctors using predetermined medical image apparatuses according to "medical order information" (*5) issued by doctors as medical workers. The medical images are image information that can be approved as a part of patient information handled in the medical support system of the present embodiment. The image information is formed, for example, including image data showing, for example, affected parts, symptoms and the like as images and "accompanying information" (*7) accompanying the image data.

The "issue" by doctors here does not refer to that the doctors do everything manually. It is possible for the doctors to confirm information generated by an issue function that information terminals have.

Issued information is not a single kind of information but includes various pieces of information. For example, information automatically formed by the system and the like are also included. For example, as an example of the issue function of information terminals, a list of patients, whom a doctor is in charge of is searched, and a patient for whom information is to be created is selected from among patient name candidates in the list. Since information about age, sex and the like is associated with the patient name selected here in advance, the doctor can input particular information without work of directly writing the patient name and accompanying information about the patient (information about age, sex and the like) only by selecting the patient name.

As for an "affected part", photographing conditions and the like, content similar to previous content may be selected without the doctor specifying the affected part, the photographing conditions and the like each time, if medical examination and diagnosis are the same as last time.

As specific situations in which the medical image is acquired, for example, following situations are conceivable:

(1) A case where a doctor as a medical worker acquires an image using a predetermined medical image apparatus himself/herself based on his/her own medical care policies (information corresponding to "medical order information" (to be described later)) (examples: an endoscopic image, an ultrasonic tomographic image and the like)

(2) A case where a doctor as a medical worker acquires an image using a predetermined medical image apparatus according to medical order information (to be described later) by another doctor (examples: an endoscopic image, an ultrasonic tomographic image and the like)

(3) A case where a medical worker (mainly a professional technician or the like) other than a doctor acquires an image using a predetermined medical image apparatus according to medical order information (to be described later) by a doctor as a medical worker (examples: an X-ray image and the like)

(*4 "Medical Reference Images)

The "medical reference images" refer to image information acquired by general medical workers who are medical workers other than doctors and professional technicians without particular qualifications to handle medical image apparatuses (for example, nurses and caseworkers; hereinafter referred to as general medical staff) and non-medical workers using "general image apparatuses" according to "medical order information" (to be described later) or "general order information" (*6) received from doctors.

The medical reference images are image information for reference with reliability enough to be recognized as patient information handled in the medical support system of the present embodiment. The medical reference images are information referred to by doctors together with regular patient information including medical images when the doctors perform a medical action.

Since the medical reference images are images acquired by general medical staff and non-medical workers as described above, the medical reference images are not approved as "medical images" as formal patient information. The medical reference images, however, are image information that can be recognized to be sufficiently reliable, as information referred to by doctors at the time of performing a medical action such as medical care. Similarly to medical images, the image information is formed, for example, including image data showing affected parts, symptoms and the like as images and accompanying information (to be described later) accompanying the image data.

(*5 "Medical Order Information")

The "medical order information" is, for example, as shown below. That is, in a normal case, after giving medical examination to a patient targeted by treatment, medical care, examination or the like (hereinafter referred to as a target patient), a doctor accesses a file server installed in a medical facility such as a hospital using a terminal apparatus in the hospital (for example, a terminal apparatus such as PC installed in a medical examination room in the hospital (a medical facility)) via a hospital network, reads out an electronic medical record file of the target patient from an electronic medical record database accumulated in the file server, and records the medical examination given on the day to the electronic medical record file. At that time, the doctor may also give one or more instructions such as an instruction of the next examination together.

In order to give the instructions, the doctor opens a predetermined order information instruction menu screen using the terminal apparatus in the hospital and creates various kinds of instruction information corresponding to a desired examination or the like from the order information instruction menu screen. In this case, a group of pieces of instruction information including instructions of specific work as a plurality of medical actions corresponding to the particular examination or the like for the particular target patient is referred to as "medical order information".

In the medical order information, for example, selection of a desired photographing item from among a plurality of photographing classifications (for example, X-ray photographing, CT, MRI, endoscopic examination, ultrasonic examination and general photographing) and selection of a desired photographing site (for example, a chest, an abdomen, a head or an elbow joint) according to the target patient are performed. In addition, a specific photographing instruction, for example, specification of the front and side of a left knee is given. Furthermore, if more detailed instructions are to be given as necessary, the detailed instructions are written, for example, in a comment field.

Here, an example of the detailed instructions in the medical order information is as follows.

For example, in the case of "medical order information for photographing images to observe the course of a wound of an affected part" about a predetermined target patient, the detailed instructions are:

(1) Photographing is to be performed in a macro mode (photographing magnification 1:2);

(2) A predetermined color chart is to be included to perform photographing so that skin color can be judged; and the like.

It is also conceivable that not only an instruction to photograph a still image but also, for example, an instruction to photograph movie or an instruction to photograph a still image or movie including voice is given.

The medical order information created as described above is associated with patient information (a patient ID and the like) about the target patient and transferred to a terminal apparatus installed in a corresponding department for handling the examination and used by a medical worker or the like belonging to the department.

Here, it is common that medical order information at a medical site is formed, including various kinds of information about "when", "where", "who" performs "which examination" "for whom" "with which apparatus", and the like.

As for "when" described above, for example, date and time information such as year, month and date corresponds.

As for "where" described above, information about a place where apparatuses and equipment corresponding to an examination to be performed are installed, such as an inside of a hospital and a related medical facility corresponds.

As for "who" described above, a medical care department or a person in charge of the examination corresponds.

As for "for whom" described above, such various kinds of information about a target patient as is written in an electronic medical record, for example, basic attribute information about the target patient such as birthday, sex and blood type, and a patient ID correspond. Such information is issued by a hospital system, a doctor or the like. However, when attention is paid to handling of personal information, it is not necessary to include all the information into the medical order information. Only information of minimum necessary items may be included.

As for "with which apparatus", an X-ray photographing apparatus, a CT apparatus, an MRI apparatus, an endoscope apparatus, an image pickup apparatus (a camera), an information terminal apparatus (such as a smartphone) or the like corresponds.

As for "which examination", it is the information about how many images are to be acquired for a site (for example, a chest or a leg) of the target patient within which range. More specifically, for example, in the case of performing general photographing of an external appearance of a predetermined affected part using an image pickup apparatus, an information terminal apparatus or the like, various kinds of photographing parameters such as composition at the time of photographing an image, a distance to an affected part, a focal length (an angle of view), photographing magnification, exposure, focus, an aperture, shutter speed, and presence/absence of auxiliary light, image quality (resolution) setting, image size setting, file format setting (compressed image, uncompressed image or the like), setting of the number of images to be photographed, and the like correspond. Note that the above information may be included in the information of the item of "with which apparatus".

As described above, the medical order information includes various pieces of information. A photographing procedure or the like for urging photographing giving display and the like so that examination and treatment can be performed according to an ordering list or the like in which the medical order information is summarized as a list and sequentially performing photographing according to the ordering list may be included. In this case, the procedure is advantageous in terms of prevention of failure to perform photographing and efficiency enhancement.

Note that the above patient basic attribute information can be also called "supplementary information for management", "supplementary information for medical care", "medical care management information" or the like.

For example, even for a same target patient, a study may be different for each of symptoms of diseases, wounds and the like, and an examination (treatment including photographing) in a different situation may be required each time. Therefore, it becomes necessary to discriminate such a study and situation each time. For example, in the case of performing health examination every year, it is conceivable to handle study information as different study information each year.

Though, in the embodiment described below, description will be made, with information as described above collectively treated as medical order information, all of the information is not always required as indispensable items for each situation unit each time. Only a part of the information required according to a corresponding situation has to be appropriately adopted.

Thus, a group of pieces of information in which one or plurality of medical action instructions are collected will be referred to as medical order information. The medical order information is created by doctors, and it is only medical workers including doctors that execute the instructions included in the medical order information in response to the medical order information.

In short, the medical order information is a group of pieces of instruction information including one or more instructions of specific work as medical actions that is created by a doctor as a medical worker and issued to medical workers (mainly professional technicians and the like) including other doctors from the doctor.

(*6 "General Order Information")

The "general order information" is a group of pieces of information issued mainly to a non-medical worker in a group of pieces of information created by a doctor as a medical worker to be provided for a particular purpose (more specifically, a group of pieces of information created by collecting one or more medical action instructions). The general order information is a group of pieces of information for particular use having content equivalent to content of the above medical order information but having a different destination. The information for particular use may be expressed as including photographing condition information and information clarifying being used for a medical action.

The general order information is a group of pieces of information created by a doctor, and content of the information may not be different from the above medical order information at all. For example, order information issued by a doctor may be an instruction that can be executed without special skills or expertise and without using special apparatuses. More specifically, for example, an instruction to photograph a general external appearance picture can be executed relatively easily even by a general non-medical worker.

A group of pieces of information including such an instruction issued by a doctor to a general non-medical worker is referred to as the general order information.

In general, even if a general non-medical worker receives the above medical order information, content of the medical order information is difficult to implement (in terms of apparatuses, expertise and qualifications) in most cases. On the other hand, since a destination target of general order information is intended to a general non-medical worker from the beginning, content of an instruction is limited.

Therefore, for example, a person who receives and executes general order information may be not a general non-medical worker but a medical worker, for example, a doctor or a professional technician. In the case where a medical worker such as a doctor receives and executes general order information, the general order information may be called medical order information. Information (for example, an image) acquired in this case can be also treated as medical information (image).

In short, general order information and medical order information are different in an assumed main receiver. Since the assumed receiver is different, content of the information differs according to the receiver.

(*7 "Accompanying Information")

The "accompanying information" described above is accompanying information that accompanies various kinds of image data. The accompanying information is integrally recorded in a predetermined area of a corresponding image data file. Accompanying information of image data of a medical image or a medical reference image handled in the present invention is configured to include, for example, in addition to basic information (for example, apparatus setting information, image format information and the like at the time of photographing) about corresponding image data, individual information of the corresponding image data (patient information, a targeted case, photographing condition information set according to an affected part, and the like). Note that the accompanying information may be in a form of being recorded as a separate file associated with a corresponding image data file.

As for examples of use of the information terminal apparatus in the medical support system of the present embodiment outside a medical facility, remote medical care, visiting medical care and home care can be assumed. In such cases, it is conceivable that an action of photographing an affected part or the like of a home patient to acquire image data is performed as one of medical actions in order to record a symptom.

For example, in the case of home medical care in which a patient stays at a place other than a medical facility, such as the patient's home, the situation is often a situation in which necessary medical apparatuses cannot be sufficiently prepared in most cases. This is because most of medical apparatuses are non-portable large-size apparatuses in a form of being fixed and used in a medical facility or the like. Even in the case of portable small-size medical apparatuses, it is difficult for a doctor or medical staff to always carry many kinds of medical apparatuses because medical apparatuses are dedicated apparatus the use of which is limited in most cases.

Therefore, in order to support home medical care, it is considered to utilize, for example, consumer products that are generally widespread (for example, various kinds of information terminal apparatuses including an image pickup apparatus such as a digital camera and an image-pickup-function-equipped smartphone). This is because, in recent years, this kind of general image-pickup-function-equipped information terminal apparatus has been commonly owned and always carried by a patient, the patients' family members and the like.

Therefore, as a quasi-medical action, at the time of attempting to perform acquisition of a patient image using such an information terminal apparatus, it is possible to ensure reliability of an acquired image even if a photographer is a non-medical worker, if information included in the medical order information described above can be used.

Further, if such general image-pickup-function-equipped information terminal apparatuses are provided in a medical facility such as a hospital, a medical worker such as a doctor or a nurse can carry and use an image-pickup-function-equipped information terminal apparatus when visiting a patient's home (at the time of medical care visiting). In this case, since it is the medical worker that operates the information terminal apparatus, reliability of an acquired image is sufficiently secured.

A concept of the medical support system of the one embodiment of the present invention assuming such a situation will be described below using FIG. 1. FIG. 1 is a conceptual diagram showing an outline configuration of the medical support system of the one embodiment of the present invention.

As shown in FIG. 1, a medical support system 1 of the present embodiment is configured mainly with a plurality of information terminal apparatuses 10 and 20, a file server 30, a network 40 provided to connect the information terminal apparatuses 10 and 20 and the file server 30 to one another.

In this case, each of the plurality of information terminal apparatuses 10 and 20 is configured to be capable of mutually performing direct communication and capable of performing data communication with the file server 30 via the network 40.

As direct communication means between the plurality of information terminal apparatuses 10 and 20, for example, existing short-distance wireless communication means (Bluetooth (registered trademark)), wired communication means (mutual communication via cable connection) or the like is applied.

As the network 40 for performing communication among the plurality of information terminal apparatuses 10 and 20, and the file server 30, for example, an existing general network such as the Internet, a dedicated network using a dedicated line, or the like can be applied.

The file server 30 corresponds, for example, to a file server included in an existing hospital information system (HIS). That is, the file server 30 is a data accumulation apparatus which is installed in a medical facility, for example, a hospital and in which various kinds of medical information including patient information are accumulated. The file server 30 is connected to the network 40 including a hospital network in the hospital and external networks such as the Internet.

The plurality of information terminal apparatuses 10 and 20 are electronic apparatuses each of which is provided with an image pickup function capable of acquiring image information and a function of communication via the network 40 in addition to a function of direct communication between the respective information terminal apparatuses 10 and 20, and each of which is configured being small-sized and portable.

As a specific form of the plurality of information terminal apparatuses 10 and 20, for example, a communication-function-equipped image pickup apparatus (such as a digital camera) or an image-pickup-function-equipped communication apparatus (such as a smartphone and a tablet PC) is assumed.

In the example shown in FIG. 1, the information terminal apparatus indicated by reference numeral 10 between the plurality of information terminal apparatuses 10 and 20 is an information terminal apparatus used by a person indicated by reference numeral 110 (for example, a doctor as a medical worker; hereinafter referred to as a doctor 110). In the description below, the information terminal apparatus is assumed to be a first information terminal apparatus and is referred to as a first terminal 10. In FIG. 1, the first terminal 10 is shown in a form of a tablet PC as an example.

The information terminal apparatus indicated by reference numeral 20 between the plurality of information terminal apparatuses 10 and 20 is an information terminal apparatus used by a person indicated by reference numeral 120 (for example, a person who is a non-medical worker such as a patient's family member or a person taking care of a patient; a medical worker is, of course, possible; hereinafter referred to as a patient's family member or the like 120). In the description below, the information terminal apparatus is assumed to be a second information terminal apparatus and is referred to as a second terminal 20. In FIG. 1, the second terminal 20 is shown in a form of a digital camera which is a general image pickup apparatus as an example.

Here, the plurality of information terminal apparatuses 10 and 20 may be in a form of a tablet PC, in a form of a camera or in other forms, for example, a form of a smartphone. No matter in which form the plurality of information terminal apparatuses 10 and 20 are, the information terminal apparatuses 10 and 20 are assumed to have basically similar functions.

That is, information terminal apparatuses (10 and 20) applicable to the medical support system 1 of the present embodiment are similarly applicable without being limited to the form the apparatuses if at least an image pickup function and a communication function are provided. Therefore, the forms of the respective information terminal apparatuses 10 and 20 shown in FIG. 1 are mere examples.

Note that, in FIG. 1, reference numeral 130 indicates a patient who is targeted by medical care. In FIG. 1, reference numeral 100 indicates a medical facility such as a hospital as a place where the doctor 110 exists. Reference numeral 200 indicates a home as a place where the patient's family member or the like 120 and the patient 130 exist.

Here, in FIG. 1, wavy lines indicated by reference numeral 300 indicate that the medical facility 100 and the home 200 exist at places away from each other.

An outline of operation of the medical support system 1 of the present embodiment configured as described above is as follows.

First, it is assumed that, for example, the patient 130 living a normal life and the patient's family member or the like 120 are in the home 200. It is assumed that the doctor 110 belonging to the medical facility 100 is a home doctor of the patient 130. It is assumed that, therefore, patient information and the like about the patient 130 are accumulated in the file server 30 installed in the medical facility 100. It is assumed that the home 200 of the patient 130 is located away from the medical facility 100.

It is assumed that, in such a situation, for example, the patient's family member or the like 120 notices something unusual on the patient 130. If the patient's family member or the like 120 can photograph an image of an unusual part (for example, an affected part) of the patient 130 using the second terminal 20 which is a general camera the patient's family member or the like 120 owns, and provide the image to the doctor 110 as a medical reference image, it will be very convenient.

However, the second terminal 20 is a general apparatus privately owned by an individual, and, as a matter of course, the second terminal 20 is not approved as a medical image apparatus. Therefore, in a normal case, such an image that is acquired using a general apparatus is not approved as a medical reference image.

Therefore, in the medical support system 1 of the present invention, such an image that is acquired by a general apparatus (the second terminal 20) is configured so that the image can be approved by the doctor 110 as a medical reference image.

As a procedure for this purpose, the patient's family member or the like 120 performs a following procedure. That is, in the situation as described above, the patient's family member or the like 120 sends request information to the effect that, since he/she wants to provide an image of the patient 130 photographed with the second terminal 20 he/she owns as a medical reference image, he/she will respond to an order if the doctor 110 issues the order, to the doctor 110. The part expressed as "request information" can be also expressed as "consultation information to doctor" or "inquiry information to doctor". From a viewpoint of the object of the present application, since the patient's family member or the like 120 is requesting an order from the doctor 110, content of the "request information" is "order request information". However, the simplified expression of "request information" is used.

The request information is information including, for example, a matter to be consulted in terms of medical care of the patient 130 and recent situation information about the patient 130. The patient's family member or the like 120 can send desired request information using the second terminal 20 to the first terminal 10 of the doctor 110 as necessary. This is because a person close to the patient 130 can feel some change in the patient 130 and because, even in such a case, the person cannot always take the patient 130 to a doctor for medical care, or the patient 130 may refuse the medical care when the patient 130 is not conscious about obvious symptoms.

In such a situation, notification of something unusual of the patient 130, consultation about whether an image of the patient 130 is to be transmitted, and the like are specifically conceivable. It is conceivable that the doctor 110 requests some specific additional information about something unusual, and the doctor 110 may request the deficient information and additional information from the patient's family member or the like 120. The request will be described below as "order information" because the doctor 110 is "requesting".

Since it is assumed that the second terminal 20 and the first terminal 10 are in an environment in which both are far away from each other in the situation described here, communication between the second terminal 20 and the first terminal 10 is performed via the network 40 as shown in FIG. 1. Note that, if the second terminal 20 and the first terminal 10 are in a short distance and can directly communicate with each other though the situation is not shown, the second terminal 20 and the first terminal 10 may perform direct communication via wireless communication or wired communication.

Note that, at the time of issuing request information to the first terminal 10 using the second terminal 20, for example, a following operation is performed. Note that though the request information is not necessarily required to be sent from the second terminal 20, the function is assumed to be a function of the second terminal 20 that performs photographing here for simplification of description. A person who performs photographing using the second terminal 20 and a person who sends a request may be different persons. For example, in the case of people related to a particular patient such as a visiting nursing team or the patient's family members, there may be a case where a person who sends request information and a photographer are different persons, and photographing is performed with a different terminal. More specifically, for example, a situation is conceivable in which a patient's wife sends request information, and the patient's son performs photographing. In this case, the request information is not necessarily required to be sent from the second terminal 20. Further, an application is also possible in which a request is sent from the second terminal 20, and received order information is transferred from the second terminal 20 to an image pickup apparatus that actually performs photographing.

First, the patient's family member or the like 120 creates request information that includes desired information to be transmitted to the doctor 110. Creation of the request information is basically performed by the second terminal 20. Since many information terminals are provided with a function capable of accepting a predetermined input operation to create a data file including arbitrary information, the function can be used if the second terminal 20 is one of information terminals of various forms such as a smartphone and a tablet terminal.

If the second terminal 20 is a general digital camera or the like, an information inputting member or the like for creating arbitrary information data is not provided in a normal case. In such a case, for example, an operation of creating request information using a smartphone, a tablet PC or the like separately owned by the patient's family member or the like 120, transferring the created request information to a digital camera used as the second terminal 20 and transmitting the request information to the first terminal 10 using a communication function of the digital camera can be performed.

Aside from the above, such means is conceivable that application software compatible with a digital camera as the second terminal 20, for example, a "medical reference image acquisition application" which is application software for handling a medical reference image is prepared and used.

In this case, a predetermined "medical reference image acquisition application" is installed in the digital camera as the second terminal 20 in advance. The application software is program software capable of causing a digital camera to operate in operation modes specialized for particular purposes, for example, a request information creation mode, a request information transmission mode, a general order information reception mode, a medical reference image photographing mode and a medical reference image transfer mode. Therefore, it becomes possible to create request information using only the digital camera as the second terminal 20 by the application software.

In this case, for example, the digital camera as the second terminal 20 is caused to operate in the request information creation mode. In the request information creation mode, for example, a list of pieces of request information included in the application (a list of assumed items of request information or the like) is displayed, and a user creates desired request information by an operation of selecting a desired item using a touch panel or the like.

A reason why a device or apparatus belonging to a category of digital camera is especially explained is that a digital camera is provided with various functions specialized in photographing and capable of easily changing photographing parameters such as composition, exposure, focus and color, and has a large degree of freedom of an angle of view and a photographing distance, and, therefore, it is possible to respond to various requests (which may be included in order information) from the doctor 110. The digital camera is good at photographing with radiation of strobe or LED illumination and is also capable of acquiring particular color information with special light. Photographing of movie includes information required by the doctor 110 in many cases, and photographing of video is also a function that the digital camera is good at. A microphone function for recording voice, heart sound, breath sound and the like is also provided. Of course, only an IC recorder may be used as the second terminal 20 when only such voice information is required.

The request information created in this way can be transmitted from the second terminal 20 to the first terminal 10 via direct communication or via the file server 30.

When the request information from the second terminal 20 arrives at the first terminal 10 of the doctor 110, the doctor 110 issues general order information according to the received request information in response to the request information. The name of "general order" is used in a sense that information acquired with a general apparatus by a general person other than medical workers is possible.

In this case, it is assumed that a "general order information creation application" which is application software specially designed to respond to a request from a general person lacking in medical knowledge is installed in the first terminal 10 in advance. The general order information creation application includes a general order information creation mode in which guidance is given so that a non-expert person can easily acquire meaningful information, a general order information transmission mode devised so that information for having a so-called consumer apparatus owned by a general person respond to such technical needs is transmitted to (or received from) the consumer apparatus and is correctly communicated to the counterpart, and the like as operation modes of the first terminal 10. For example, in order to perform exchange by telephone, e-mail or SNS, reception is also required. Therefore, the general order information transmission mode may be expressed as a general order information communication mode.

When receiving the "request", the doctor 110 considers necessity to request additional information and operates the first terminal 10 to communicate whether the additional information is necessary or not to the request sender. In such a case, since the counterpart may make a counterargument, it is important to perform exchange (the general order information communication mode or a general order information transmission/reception mode). For example, subtle nuance is not communicated only by text-based information such as an e-mail, and it becomes impossible to make a correct judgment or a response depending on whether sentences are good or not. Therefore, there is a possibility that a necessary order cannot be issued.

At this time, in a case where the doctor 110 judges that more accurate information and additional information are required, it is necessary that the information is information that can be acquired by a general person with a general consumer apparatus. Therefore, the general order information creation application designed in consideration of the above is activated, and a predetermined operation is performed to create general order information (the general order information creation mode). Then, the created general order information is transmitted to the second terminal 20 (the general order information transmission mode).

The order here must not require a special qualification, a special apparatus and the like for an X-ray examination or the like. Simple information about such an auxiliary examination or a reference examination that substitutes for the X-ray examination or the like is to be ordered. Therefore, it is assumed that an operation is performed with a user interface (UI) with such icon design and a menu configuration that only such an order can be selected.

Since the patient's family member or the like 120 is not a medical-related person in many cases, description is made on the assumption that the patient's family member or the like 120 is a general person. The patient's family member or the like 120 receives the general order information created for general persons using the second terminal 20 (the general order information reception mode). It is necessary that the general order information is created by replacing technical medical terms with general terms understandable to persons other than medical workers. If not, the patient's family member or the like 120 cannot understand which and how he/she should respond to even if he/she receives the order information.

An order of the doctor 110 adapted so that only a simple order (instruction), such as an instruction to take a picture of a position (an affected part of the patient 130 or the like) after confirming the patient 130 is the patient himself/herself, is included. This is because the "general order information creation application" is devised and designed as such. That is, the "general order information creation application" is designed so that such an order that is difficult for a general person to execute cannot be given. When the doctor 110 issues a difficult order, the application replaces difficult terms with simple terms or changes a method to a simple method so that everyone can respond to the order. In a case where such a response is impossible, the "general order information creation application" does not issue an order or causes content of an instruction, such as "Entrust everything to expert without doing anything", to be generated.

As an example of simplification of work, an order can be devised so that some settings are to be gradually made. Photographing order at the time of sequentially photographing a whole body and an enlarged part so that a site can be recognized in a whole body image is included in order information. As an example of a specific utilization technique, artificial intelligence and the like are given. The "general order information creation application" described above includes a function of, even if the doctor 110 uses a medical term, converting the medical term to a general term. More specifically, a database for term conversion, an inference engine by artificial intelligence or the like is adopted. The database, the inference engine or the like may exist on either the first or second terminal or may exist on the network connecting the first and second terminals.

Of course, an apparatus such as a camera may be provided with such artificial intelligence and the database function. Since the devices as described above are made, a request (order) of the doctor 110 is replaced with such that everyone can respond to or a simple instruction that can be immediately understood by a general person, such as an advice of entrusting everything to an expert, and displayed, or is communicated by voice. Therefore, by using or referring to such guidance, it becomes possible for the patient's family member or the like 120 to make a response according to the order and performing desired photographing of the patient 130 using the second terminal 20 (the medical reference image photographing mode).

Predetermined information included in the general order information is recorded to image data of the patient 130 photographed using the second terminal 20, which is a general apparatus or device, in response to the request of the doctor 110 as accompanying information. Thus, the image data is consequently created as image data provided with a predetermined format to be approved as a medical reference image.

That is, the patient's family member or the like 120 is worried or feels anxious about a situation of the patient 130, and sends desired request information (in which information about apparatuses, tools and the like that he/she can currently use may be written) to the doctor 110, the request information indicating that he/she wants to be told if there is anything that he/she can do, in a manner of consulting the doctor about which information else he/she should send. Receiving the request information, the doctor 110 considers the situation and issues appropriate general order information according to his/her judgment, it becomes possible for the general apparatus (the second terminal 20) having received the general order information to acquire a medical reference image that is required by the doctor 110 and is worth managing in the hospital or evaluating as medical information.

Then, the medical reference image (not limited to an image but may be voice or other information such as temperature, weight and blood pressure) acquired in this way is recognized as responding to the order of the doctor 110. A judgment of the doctor 110 who has received the medical reference image is taken into account, and a predetermined quality as a medical reference image is secured.

It is preferable that there is accompanying information such as information about in which situation information, which kind of information about which patient has been acquired by which apparatus in which way of using the apparatus. If what are included in the order information described above are used as some of such pieces of information, it will be efficient. The image data is transferred from the second terminal 20 to the file server 30 or the like and accumulated as a part of patient information about the target patient 130.

Thus, the present embodiment includes a novel invention as described below. It is preferable that request information is such information that a doctor appropriately issues an order based on a correct judgment and is information in which a patient's family member or the like can input or select apparatuses, devices, systems, tools and the like that can be used by the patient's family member or the like then.

For example, if there is a camera and a ruler, it is possible to apply a ruler to a wound and photograph an image including information about the size. If a communication system has a particular performance and is stable, diagnosis using a streaming image and diagnosis by a TV conference become possible.

Skill information about the patient's family member and, if a picture is to be sent, information about a photographing technique acquisition level are also effective. A same instruction differs according to whether an order is given by an expression of "by decreasing the aperture" or by an expression of "by operating the dial of a camera". Which expression is more understandable and enables work to be done more quickly is different according to a receiver who receives the instruction.

It is difficult for a doctor to determine which of some such order candidates is to be selected unless sufficient judgment material is included in request information. That is, the above request information may include information about a target patient and a user himself/herself who uses an information terminal apparatus and may include information about apparatuses that the user using the information terminal apparatus can use. The above request information may include skills information about the user using the information terminal apparatus. The skills information may be any of skills information such as sex, age, physical condition, language ability and sentence ability, and information about setting ability of communication and networks and so on, in addition to information about ability to master and use apparatuses and tools (information terminal apparatus may be included). There is a possibility that items that a doctor can request may differ according to the information.

As described before, order information also must be written in simple expressions and communicated to a counterpart so that a general person can respond to a doctor's request (order) using general apparatuses or tools. For this purpose, it is required to utilize a graphic user interface accompanied by illustration, give a specific instruction showing illumination conditions and distance conditions, dividing what could be very briefly explained to an expert to a plurality of steps to explain each step, or provide a guidance that is interactively implemented, according to a situation or a difficulty level.

That is, in other words, the above guidance information can be guidance information changed according to the request information. That is, the present invention can be said to be a proposal of a patient information acquisition method for acquiring information about a target patient including: receiving information about the target patient and request information including information about apparatuses that can be used by a user, creating guidance information according to the request information, and acquiring additional information acquired according to the guidance information, and can be said to be an invention of a system including an apparatus for achieving the method. The above is an expression without expressions of a first terminal and a second terminal. However, a similar problem can be similarly solved by using same apparatuses. This is because such a modification as below is conceivable. For example, when a patient's family member hands over a terminal to a doctor, a request is recorded in the terminal. The doctor who has seen the request returns the same apparatus to the patient's family member, the patient's family member acquires information facing the patient, seeing a guidance displayed on the terminal (according to an order).

For example, such a solution as above is conceivable for a patient's family member who can usually come to a hospital only in the daytime to consult a night shift doctor. In a case where a doctor is in a regular daily work form, and a patient's symptoms appear at midnight, a similar solution method can be adopted. Such a method can be realized by providing a system, an apparatus and the like for realizing the idea.

Note that though the example shown in FIG. 1 shows an example of the patient's family member or the like 120 using the second terminal 20, the present embodiment is not limited to the illustration. The second terminal 20 is similarly used in a situation of being used by the patient 130 himself/herself. The basic schematic operation of the present embodiment is as described above.

If such conditions are included in request information, there is a possibility that a judgment made by a doctor changes. For example, it is difficult for a patient himself/herself to photograph a picture of his/her back or the like. Whether it is difficult for the patient to photograph a picture of his/her back or the like also depends on whether there is a mirror (corresponding to one of the tools described above). Including such a case, various modifications of a relationship between a request sender and a photographer are possible. There may be a situation in which a patient worries about himself/herself and issues a request and asks another person to perform photographing according to the request.

Next, operation of the medical support system 1 of the present embodiment will be briefly described for each specific use situation (use pattern).

Figure 2:
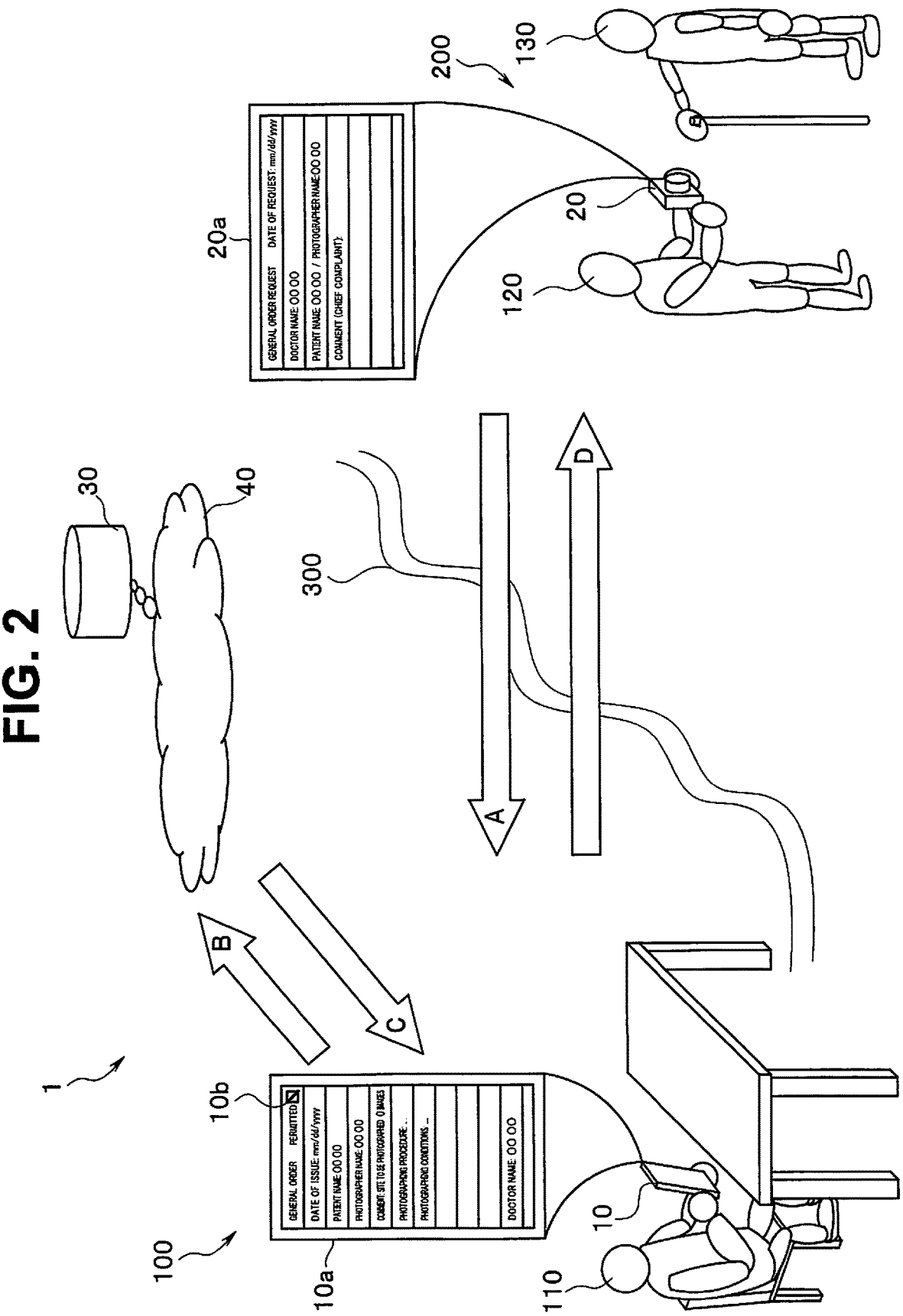
FIG. 2 is a conceptual diagram illustrating a first use pattern of operation of the medical support system of the one embodiment of the present invention.
Figure 3:
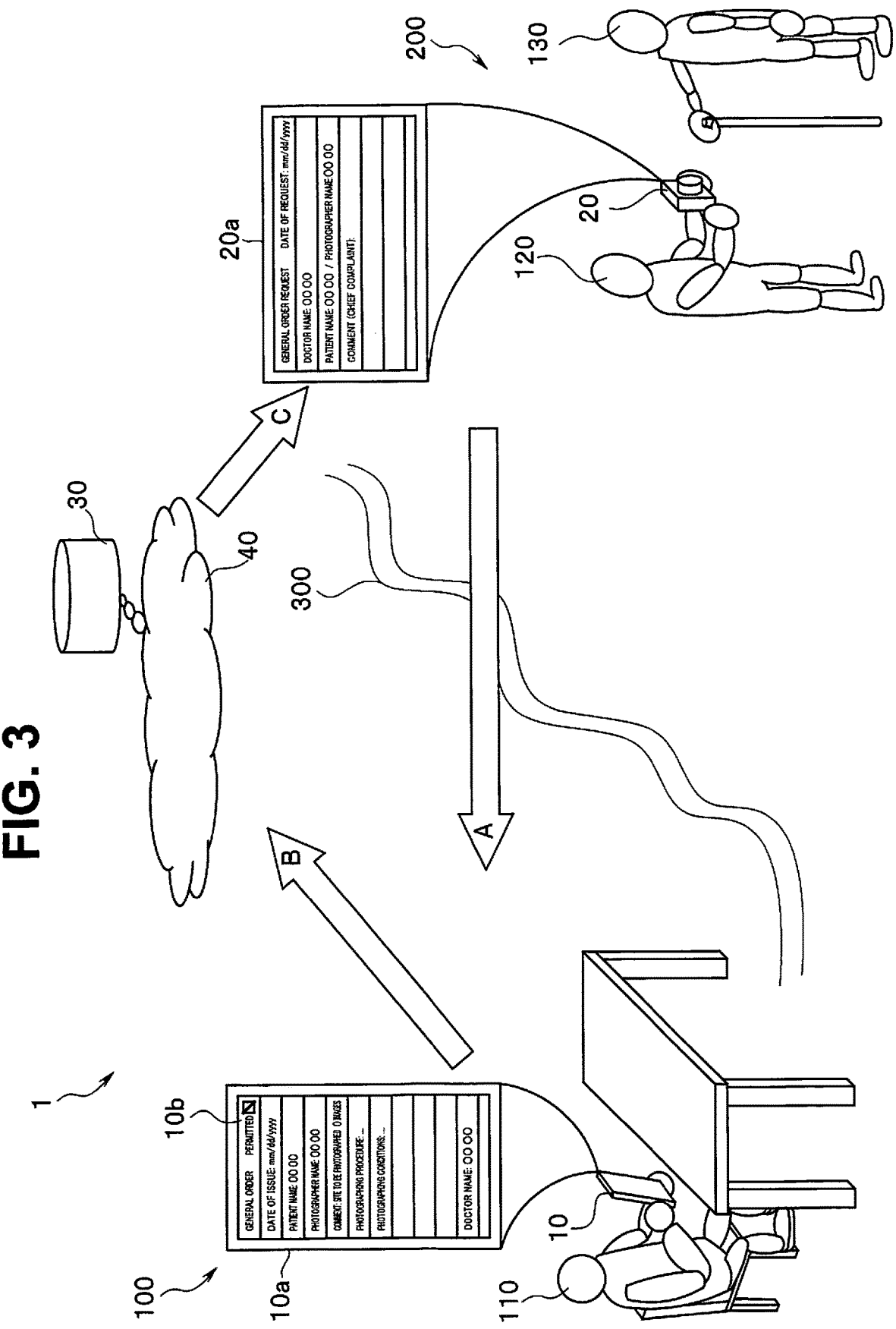
FIG. 3 is a conceptual diagram illustrating a second use pattern of operation of the medical support system of the one embodiment of the present invention.
Figure 4:
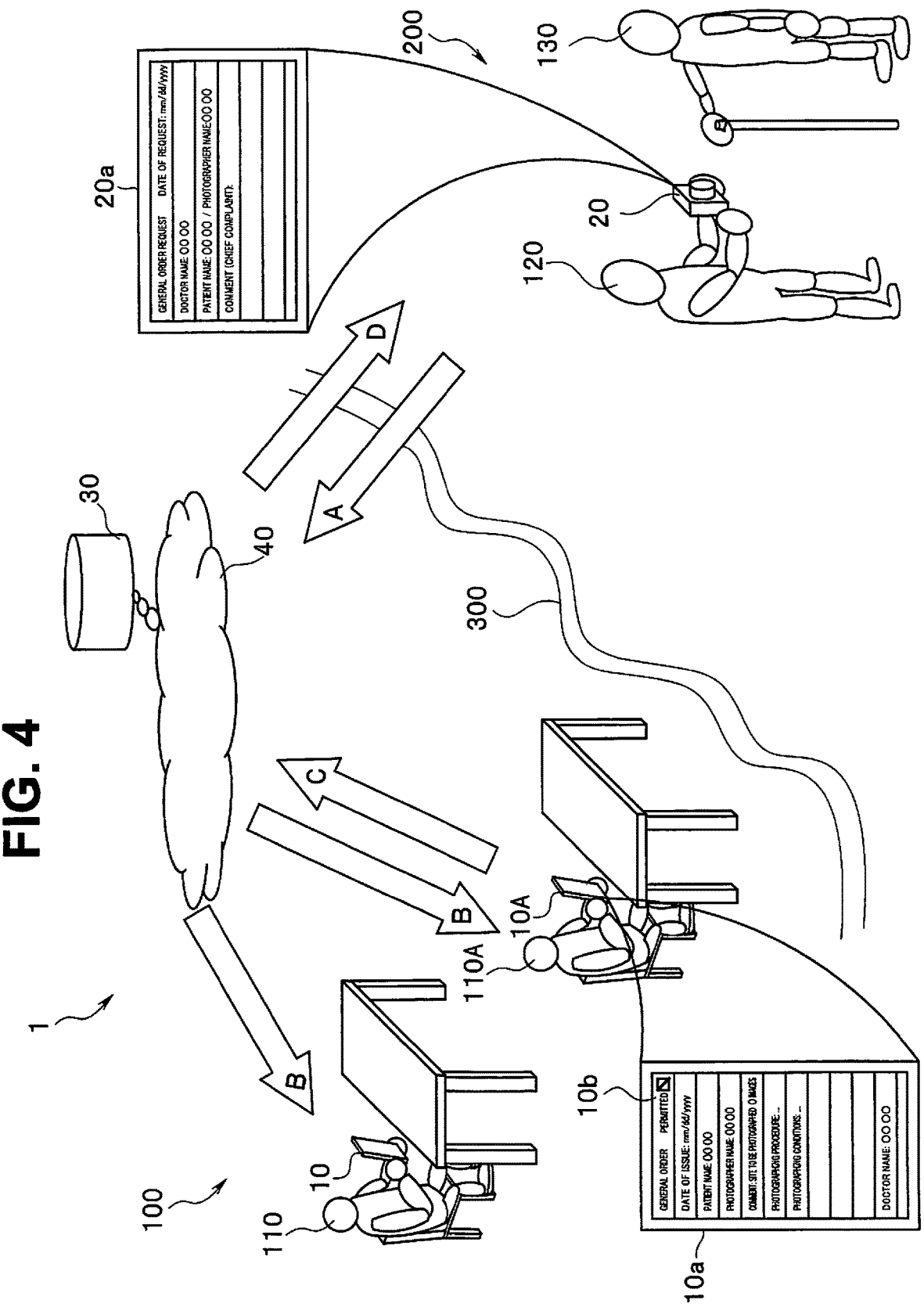
FIG. 4 is a conceptual diagram illustrating a third use pattern of operation of the medical support system of the one embodiment of the present invention.

FIGS. 2 to 4 are conceptual diagrams showing an outline of the operation of the medical support system of the present embodiment according to use situations. Among FIGS. 2 to 4, FIG. 2 is a conceptual diagram illustrating a first use pattern of the operation of the medical support system of the present embodiment. FIG. 3 is a conceptual diagram illustrating a second use pattern of the operation of the medical support system of the present embodiment. FIG. 4 is a conceptual diagram illustrating a third use pattern of the operation of the medical support system of the present embodiment.

([First Use Pattern])

First, the first use pattern of a use situation of the medical support system 1 of the present embodiment is as follows (see FIG. 2). Here, the first pattern assumes a case where a relationship between a doctor as a home doctor, for example, of a clinic (a privately managed small-scale medical facility) and a patient (including the patient's family members) is relatively strong.

First, the patient's family member or the like 120 performs direct communication with the first terminal 10 of the doctor 110 to transmit request information using the second terminal 20 (arrow reference symbol A in FIG. 2: the request information transmission mode).

In this case, it is assumed that a terminal to receive the request information is the first terminal 10 of the doctor 110, but the terminal is not limited to the first terminal 10. For example, if it is the medical facility 100 that manages the first terminal 10, it is not only the doctor 110 who directly receives the request information that receives the request information first using the first terminal 10. There may be a case where such a procedure occurs that a receptionist in the medical facility 100 (a general medical worker, for example, a nurse or a qualified medical clerk) performs a reception operation and then communicates the request information to the doctor 110. Here, the doctor 110 is illustrated as a representative example of a receiver in the medical facility 100 for simplification of description.

Note that even if the first terminal 10 receives the request information from the second terminal 20, the doctor 110, the receptionist or the like does not necessarily immediately confirm the request information that has arrived at the first terminal 10. Therefore, after transmitting the request information from the second terminal 20, the second terminal 20 is in a state of waiting for a response from the first terminal 10.

Here, as content of the request information sent from the second terminal 20, there are, in addition to basic information such as a title of "General Order Request", a request year, month and date, a destination doctor name, a patient name and a photographer name, chief complaint information and the like as comments, for example, as indicated by reference numeral 20a in FIG. 2. As the main complaint information, a reason to transmit the current request information, a matter to be consulted in terms of medical care of the patient 130, recent situation information and the like about the patient 130 can be specifically shown.

The request information sent from the second terminal 20 is received by the first terminal 10. The doctor 110 confirms the received request information using the first terminal 10, for example, when he/she has time.

The doctor 110 who has confirmed the request information accesses the file server 30 using the first terminal 10 (arrow reference symbol B in FIG. 2) and refers to medical record data and the like about the target patient 130 of the received request information (arrow reference symbol C in FIG. 2).

The doctor 110 creates general order information according to the received request information using the first terminal 10. After that, the doctor 110 directly connects to the second terminal 20 using the first terminal 10 and sends the created general order information to the second terminal 20 (arrow reference symbol D in FIG. 2).

Here, as content of the general order information created on the first terminal 10, there are, in addition to basic information such as a title of "General Order", an issue year, month and date, the patient name, a patient ID (patient-specific identification information), the photographer name, and an issuer name (information about doctors in charge and the medical institution including the name of a doctor in charge), various kinds of information (a site specified to be photographed, the number of images required, a photographing procedure, photographing conditions and the like) according to the chief complaint as comments, for example, like a display screen indicated by reference numeral 20a in FIG. 2. Note that, here, the photographing conditions include, for example, a photographing format (a file format), various kinds of settings such as image aspect ratio information, and instruction information such as an instruction to include a scale in a screen. Furthermore, as the photographing condition information, setting information and the like about various kinds of photographing parameters and the like to enable an equal and similar image to be photographed at each time of photographing, and thumbnail images of sample images, and the like are also included.

Note that the above setting information includes various kinds of image pickup related information, for example, exposure information, white balance information, sensitivity information, optical system focal length information, information about a distance to an object, photographing magnification information and angle information.

In addition to the above, various kinds of information included in Exif image data or the like that has been conventionally used as a common image file (for example, a photographing place (GPS information), date and time information and photographing condition information) may be included in medical metadata.

Furthermore, approval information as a medical reference image is attached to general order information. In the form example shown in FIG. 2, an icon display indicating "permitted" and a permission display 10b in a form of a check mark being inputted are shown.

When receiving such general order information (the general order information reception mode), the second terminal 20 displays the content of the general order information on the display screen, for example, in a form equivalent to the form indicated by reference numeral 10a in FIG. 2 (note that reception by the second terminal 20 is not shown (see reference symbol 10a in FIG. 2).

Then, the patient's family member or the like 120 as a photographer executes photographing of the patient 130 according to the received general order information using the second terminal 20.

The second terminal 20 may be provided with a predetermined photographing operation mode for, at the time of performing photographing according to general order information, automatically making various kinds of settings and the like so that an appropriate photographing operation can be easily executed. A photographer can perform appropriate photographing only by switching to the predetermined photographing operation mode. Here, as the predetermined photographing operation mode, for example, the "medical reference image photographing mode" or the like is assumed. As for the medical reference image photographing mode of the second terminal 20 in this case, for example, a corresponding application can be also installed in the second terminal 20 in advance.

To image data acquired in this way, various kinds of information included in the general order information is recorded as accompanying information.

In this case, an image data file handled in the medical support system 1 of the present embodiment has, for example, predetermined metadata including medical information separately from ordinary metadata (referred to as general metadata) included in a conventional general image data file (for example, an Exif (exchangeable image file format) data file or the like), and the predetermined metadata is especially referred to as medical metadata.

Note that the medical metadata may be configured to exist in a form of a file separate from the conventional general metadata or may be integrally configured. However, no matter which form is adopted, it is important that the image data and the metadata are associated with each other. By the image data and the medical metadata being associated with each other, a predetermined operation is necessarily performed being accompanied by the associated metadata at the time of performing an operation on the image data (for example, an operation of movement to another medium, copying or deletion), even if each of the image data and the metadata exists as a single data file. Therefore, for example, it does not happen that only the medical metadata exists alone.

As for the medical meta data, in addition to the information included in the general order information inputted by the doctor 110 as described above, for example, items overlapping with the existing general metadata, for example, information about a date and time at the time of photographing and photographing apparatus information (such as camera-specific information) are automatically added.

If it is not for the first time that the first terminal 10 receives the request information from the second terminal 20 of the particular patient's family member or the like 120, but there are use results in the past, then request information received before should already exist in the first terminal 10.

Therefore, when the first terminal 10 receives the request information from the second terminal 20 as described above, for example, corresponding patient information (for example, a patient ID) can be automatically detected. Therefore, using the patient information detected by the first terminal 10, the doctor 110 can automatically and quickly search for desired information in the file server 30.

Then, the image data acquired using the second terminal 20 is transferred to the file server 30 by some means though it is not shown (the medical reference image transfer mode). That is, for example, the image data is transmitted from the second terminal 20 to the file server 30 via the network 40 and recorded to a predetermined area in the file server 30. At this time, the image data is associated with patient information about the target patient 130 among a plurality of pieces of patient information recorded in the file server 30, as information related to the patient information about the target patient 130.

The acquired image data is recorded to the file server 30 via a reception department or provided to the first terminal 10 of the doctor 110 by the patient's family member or the like 120 or the patient 130 visiting the medical facility 100 carrying the second terminal 20.

By the predetermined medical metadata included in the general order information being given to the image data acquired by the second terminal 20 in this way, the image data can be handled as a medical reference image approved by the doctor 110. Therefore, the doctor 110 can refer to the image data as a medical reference image for medical care.

Note that though it is described in the description above that the various kinds of information related to photographing (the photographing condition information) is included in the medical metadata, the present embodiment is not limited to the above. The photographing condition information may be created, for example, as a data file separate from an image data file. The data file of the photographing condition information is recorded in association with a corresponding image data file. Therefore, when image data is transferred to another apparatus, a related photographing condition information data file is necessarily transferred together with the image data at the same time as a set.

As described above, such a method that photographing condition information is added into an image file as metadata is thought, and the present invention also proposes an apparatus, a device, a method and the like for creating such a new image file. It is not necessary to include all of the photographing condition information into metadata, and a part of the photographing condition information may be included. The present invention also proposes an apparatus, a device, a method and the like for creating a new image file having metadata of information to be associated with photographing condition information.

It is also possible to create a new image file and simultaneously create medical metadata corresponding to image data of the image file as a separate file. In this case, it is possible to associate the image file and the corresponding metadata file with each other even if specifications specify that the image file and the corresponding metadata file are always not sent together as a set.

That is, specifications specifying that an image file should be sent after transmission of a photographing condition information data file (or reverse order) may be adopted. It is also conceivable that the medical support system 1 requests such transmission that performs association with a photographing condition information data file, and a related image is sent in response to the request so that an image file and metadata are associated with each other on the support system side (the file server 30 or the like).

When the patient's family member or the like 120 performs predetermined photographing of the patient 130 using the second terminal 20 that has received general order information, identification information for identifying the patient 130 may be recorded.

As for the identification information, for example, at the time of photographing the patient 130 facing the patient 130, confirmation is performed by calling the patient 130 to cause the patient 130 to give his/her name. For this purpose, the second terminal 20 is provided with a configuration for recording voice for the confirmation (a microphone and a voice recording portion). Voice data recorded then is associated with image data acquired after that.

In order to avoid impersonation by voice, video may be photographed to record a state of confirmation by conversation to be used as evidence. Since confirmation that should be essentially done by a doctor or a medical worker in charge is entrusted to a terminal apparatus and an operator, preservation of evidence is important. Therefore, it is better to record which doctor order at which point of time identification is based on. In the case of requiring further strictness, a doctor's terminal, and a communication line such as a telephone line, or a network may be used only then to cause a doctor or a medical worker to directly talk with a patient and record the talk.

As for the identification information, a face recognition technique that the second terminal 20 is provided with can be used. Here, as the second terminal 20, an information terminal apparatus owned by a family member or a relative of the patient 130 or the patient 130 himself/herself is assumed. Therefore, a face image of the patient 130 himself/herself is registered with the second terminal 20 in advance. By performing photographing using the second terminal 20, it can be easily detected that the patient 130 himself/herself is targeted by photographing.

When detecting the patient 130 himself/herself as described, the second terminal 20 may judge that photographing of a medical reference image is to be performed and perform control to automatically switch to a corresponding predetermined photographing operation mode (the medical reference image photographing mode).

When the second terminal 20 switches to the medical reference image photographing mode, a controlling portion (to be described later) of the second terminal 20 refers to the photographing condition information and the like included in the received general order information to perform control to automatically set photographing parameters (such as an exposure setting, a white balance setting, a sensitivity setting and a focal length setting) optimal to acquire a new medical reference image. At this time, a guidance display (an assist display) of photographing condition information such as composition, a photographing angle and a distance to an object is automatically displayed in a display portion. As for the display, for example, a form of superimposed display on a live view image on the display portion is conceivable.

Note that though description has been made above with the patient's family member or the like 120 as a person who issues request information and is a photographer as an example, the present embodiment is not limited to the example. For example, when a situation of a doctor's visiting medical care, visiting nursing care or the like is considered, a corresponding person in that situation is similarly applicable as a photographer facing the patient 130. In that case, a nurse, a care worker or the like visiting the patient's home corresponds to a person who operates the second terminal 20.

In this way, it is possible to cause image data acquired by a general medical worker or a patient's family member or the like 120 other than medical workers using a general information terminal apparatus (the second terminal 20) to be handled as a medical reference image that can be approved by the doctor 110.

The outline of the first use pattern of the use situation of the medical support system 1 of the present embodiment is as described above. Thus, according to the present invention, a non-medical worker can easily obtain reliable image information to be an aid to medical care and diagnosis for a doctor at a remote place, using a general terminal such as a camera or a smartphone.

([Second Use Pattern])

Next, the second use pattern of the use situation of the medical support system 1 of the present embodiment is as follows (see FIG. 3). Here, basically, the second use pattern is almost similar to the first use pattern. The second use pattern described below is different in a point that details of creation of general order information are not performed by a doctor but by automatic processing by the system.

It is the same as the first use pattern described above that the patient's family member or the like 120 creates request information using the second terminal 20 first (the request information creation mode) and performs direct communication with the first terminal 10 of the doctor 110 to transmit the request information (arrow reference symbol A in FIG. 3; the request information transmission mode). Content of the request information sent from the second terminal 20 at this time is also similar to the content described for the first use pattern above.

When confirming the request information received by the first terminal 10, the doctor 110 accesses the file server 30 using the first terminal 10 to issue predetermined instruction information according to the target patient 130 of the received request information to the file server 30 (arrow reference symbol B in FIG. 3).

The instruction information issued from the doctor 110 here is only basic information including the request information, and a very simple instruction according to the patient 130.

Receiving the instruction information of the doctor 110, a controlling portion (to be described later) of the file server 30 creates general order information according to the request information. After that, the file server 30 sends the created general order information to the second terminal 20 (arrow reference symbol C in FIG. 3). The second terminal 20 receives the general order information (the general order information reception mode). After that, predetermined photographing is performed according to the received general order information (the medical reference image photographing mode). Then, image data of a photographing result is transferred to the file server 30 (the medical reference image transfer mode).

Content of the general order information created by the file server 30 here is similar to the content described for the first use pattern above.

Operation of the second terminal 20 which has received the general order information is also similar to the operation in the first use pattern.

Thus, the second use pattern is the same in the point that it is possible to cause image data acquired by a general medical worker or a patient's family member or the like 120 other than medical workers using a general information terminal apparatus (the second terminal 20) to be handled as a medical reference image that can be approved by the doctor 110.

Further, in the second use pattern, by entrusting the general order information creation processing to automatic processing by the file server 30, it is possible to simplify doctors' manual work and, therefore, reduce a burden on the doctors.

Note that though in the description of the second use pattern above, description is made on an assumption that the controlling portion of the file server 30 creates general order information according to request information, the present embodiment is not limited to the example. For example, the instruction information from the doctor 110 may be transferred to an information processing apparatus such as a PC (not shown) installed in the reception department in the medical facility 100 via the file server 30 so that the general order information creation processing may be performed by the information processing apparatus of the reception department and a receptionist who handles the information processing apparatus.

The general order information created by the automatic processing or by the receptionist in the second use pattern may not be sent to the second terminal 20 immediately after being created but may be confirmed by the doctor 110 once before being sent after creation. By doing so, reliability of the general order information can be further enhanced.

The outline of the second use pattern of the use situation of the medical support system 1 of the present embodiment is as described above. Thus, according to the present invention, a non-medical worker can easily obtain reliable image information to be an aid to medical care and diagnosis for a doctor at a remote place, using a general terminal such as a camera or a smartphone.

([Third Use Pattern])

Next, the third use pattern of the use situation of the medical support system 1 of the present embodiment is as follows (see FIG. 4). Here, basically, the third use pattern is almost similar to the first use pattern and the like. The third use pattern described below assumes a case of being operated, for example, in a medical facility such as a large-scale hospital provided with a lot of doctors and a fully equipped hospital system.

In this kind of large-scale medical facility, work generally starts after passing through a reception system first. As for doctors responding to a particular patient, it is common that a team including a plurality of doctors is systematically in charge of the particular patient. Therefore, a particular doctor is not always in charge of a particular patient. There are many patients that one doctor is in charge of.

Therefore, if information related to a plurality of patients that a particular doctor in charge of is directly transmitted to the doctor's first terminal 10, it is naturally impossible for the reception-side doctor to respond to all the information. In consideration of the above, all request information sent from a patient side is accumulated in the file server 30 via the reception department of the hospital system first in the third use pattern (arrow reference symbol A in FIG. 4).

When request information is inputted to the file server 30, the file server 30 refers to information included in the request information and simultaneously delivers the request information to a plurality of doctors in charge (arrow reference symbol B in FIG. 4).

Note that though two persons indicated by reference symbols 110 and 110A are shown as the plurality of doctors in charge in the example shown in FIG. 4, more doctors may exist.

The plurality of doctors in charge (110, 110A . . . ) confirm the request information at different timings, for example, because of difference in working hours or being engaged in other work (for example, performing an operation). Therefore, for example, one doctor (in the example shown in FIG. 4, a doctor indicated by reference symbol 110A) who can confirm the request information first, among the plurality of doctors in charge (110, 110A . . . ) responsible for a target patient of the request information, creates general order information.

Here, a procedure for the doctor 110A to create the general order information is similar to the procedure described above for the first use pattern. The general order information created by the doctor 110A in this way is transferred to the file server 30 and recorded in association with the target patient (arrow reference symbol C in FIG. 4).

At this time, when the general order information according to the request information is created and registered with the file server 30, the file server 30 sends status (situation state) information indicating "having been processed" to the other doctors to whom the relevant request information has been simultaneously delivered (in the example shown in FIG. 4, the doctor 110). By doing so, it is possible to prevent duplicated processing that a plurality of pieces of general order information are created for a certain one piece of request information.

The general order information registered with the file server 30 is transmitted being addressed to a sender (the second terminal 20) of the corresponding request information after passing through the reception department.

According to such a configuration, it is also possible to similarly apply the present embodiment in a large-scale medical facility and obtain similar effects.

The outline of the third use pattern of the use situation of the medical support system 1 of the present embodiment is as described above.

In order to realize the operation as described above, main components of the information terminal apparatus (the first terminal 10 and the second terminal 20) and the file server 30 of the medical support system 1 of the present embodiment will be described below.

Figure 5:
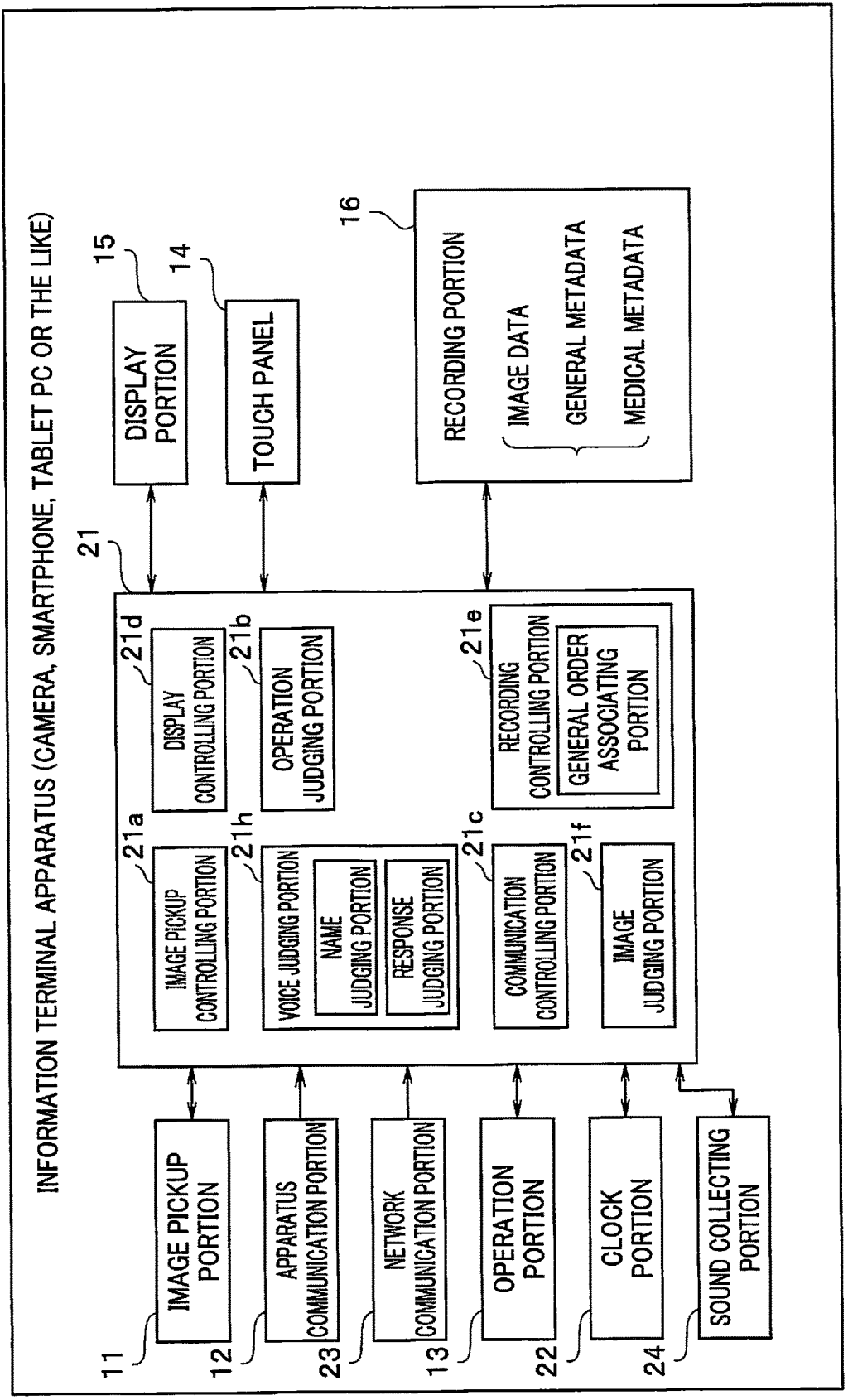
FIG. 5 is a block configuration diagram showing main components of an information terminal apparatus in the medical support system of the one embodiment of the present invention.
Figure 6:
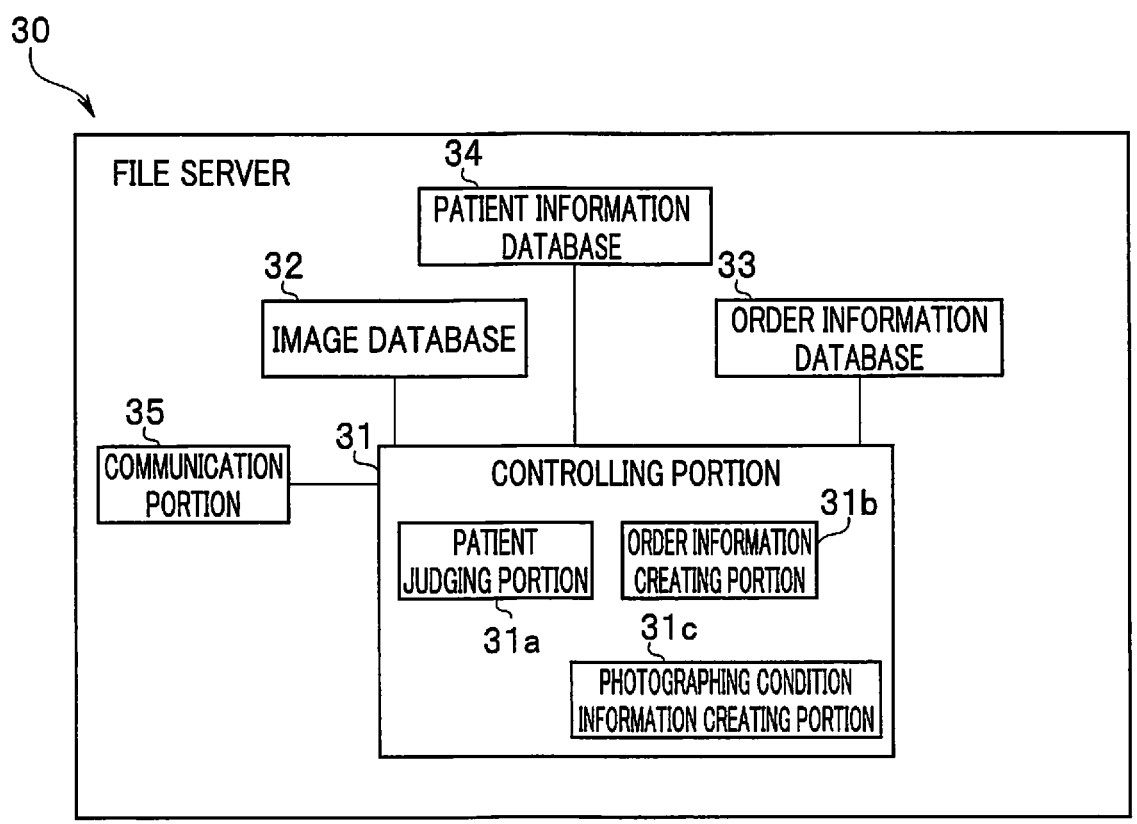
FIG. 6 is a block configuration diagram showing main components of a file server in the medical support system of the one embodiment of the present invention.

FIG. 5 is a block configuration diagram showing main components of the information terminal apparatus in the medical support system of the present embodiment. FIG. 6 is a block configuration diagram showing main components of the file server in the medical support system of the present embodiment.

First, the main components of the information terminal apparatuses (10 and 20) in the medical support system 1 of the present embodiment will be described. As described above, the information terminal apparatuses are the first terminal 10 used by a doctor and the second terminal 20 used by a person other than a doctor (for example, a medical worker other than a doctor, or a patient's family member). The main components of the information terminal apparatuses are almost similar even if forms of the information terminal apparatuses are different. Therefore, description will be made below on an assumption that the first terminal 10 and the second terminal 20 have the same components.

As shown in FIG. 5, the information terminal apparatus (10 or 20) is configured mainly being provided with an image pickup portion 11, an apparatus communication portion 12, a network communication portion 23, an operation portion 13, a touch panel 14, a display portion 15, a recording portion 16, a sound collecting portion 24, a clock portion 22, an image processing controlling portion 21 and the like.

Note that, as components of the information terminal apparatus (10 or 20), various components are provided in addition to the components enumerated here. However, since the components are not directly related to the spirit of the present invention, the components are not shown or described. It is assumed that, as for the various kinds of components that are not shown or described, components similar to components applied to an information terminal apparatus in a conventional general form are provided.

The image pickup portion 11 is a component unit including an optical system configured to form an optical image and a circuit or the like including a photoelectric conversion element or the like configured to convert an optical object image formed by the optical system to an electrical signal, and configured to realize an image pickup function.

Note that, as for specific components of the image pickup portion 11, components almost similar to components of an image pickup unit in a conventional general form are applied. The image pickup portion 11 is controlled by an image pickup controlling portion 21a to be described later.

The apparatus communication portion 12 is a component unit configured including a circuit unit configured to realize communication performed between apparatuses (for example, short-distance wireless communication means).

The network communication portion 23 is a component unit configured including a circuit unit configured to realize communication with the file server 30 via the network 40.

Note that the communication means included in the apparatus communication portion 12 and the network communication portion 23 is not limited to wireless communication means, but wired communication means is also included. The apparatus communication portion 12 and the network communication portion 23 are controlled by a communication controlling portion 21c to be described later.

In the second terminal 20, the apparatus communication portion 12 and the network communication portion 23 (generically referred to as communication portions) have a transmission function of transmitting request information to the first terminal 10 or the file server 30 as well as a reception function of receiving general order information sent from the first terminal 10 or the file server 30.

The operation portion 13 is a component unit including an operation member and a circuit portion for, in response to various kinds of operations performed by a user, causing corresponding various kinds of instruction signals to be generated.

The touch panel 14 is an operation member arranged in a form of being superimposed on a display screen of the display portion 15. The touch panel 14 is an operation member configured to, in response to operation instructions by the user's finger or the like, cause corresponding various kinds of instruction signals to be generated.

Note that though the touch panel 14 is included in the operation portion 13, the touch panel 14 is shown separately from the operation portion 13 because the touch panel 14 is one of operation members often applied in various electronic apparatuses nowadays and is an especially important component.

Which of the operation portion 13 and the touch panel 14 has been operated is judged by an operation judging portion 21b to be described later. Based on a result of the judgment, the image processing controlling portion 21 outputs a corresponding predetermined operation signal to a corresponding component unit.

The display portion 15 is a component unit including a display panel and a driving circuit for the display panel and the like (not shown) and configured to realize a display function. On the display panel of the display portion 15, an image based on image data acquired using the image pickup portion 11 and menu images generated by various kinds of setting programs and the like are displayed. The display portion 15 is controlled by a display controlling portion 21d.

The recording portion 16 is a component unit for recording various kinds of data files. As data files recorded to the recording portion 16, there are, for example, image information including image data and metadata (general metadata and medical metadata), setting information which is a filed in which various kinds of settings such as settings specific to setting items required at the time of performing predetermined photographing are collected (more specifically, for example, setting information in which various kinds of settings to be made at the time of acquiring a medical reference image are collected), apparatus information and the like about the information terminal apparatus (10 or 20) and communication counterparts' apparatuses (a terminal, a file server or the like) and other various kinds of information. To the recording portion 16, voice data acquired by the sound collecting portion 24 is also recorded.

The clock portion 22 is an internal clock circuit that is called a so-called real time clock (RTC). The clock portion 22 is a circuit portion used, for example, at the time of giving date and time information and time information to an image file, measuring a time period between predetermined instruction timings during control processing, and performing temporary control.

The sound collecting portion 24 is a component unit including a microphone, a driving circuit for the microphone, and the like and is configured to collect voice data. The sound collecting portion 24 is controlled by the image processing controlling portion 21. Various kinds of judgments by a voice judging portion 21h are made based on the voice data acquired by the sound collecting portion 24. The voice data acquired by the sound collecting portion 24 is recorded to the recording portion 16.

The image processing controlling portion 21 is a control circuit configured to comprehensively control the information terminal apparatus (10 or 20) and is an image processing circuit configured to perform various kinds of image processing based on various kinds of image data.

The image processing controlling portion 21 is configured being provided with the image pickup controlling portion 21a, the operation judging portion 21b, the communication controlling portion 21c, the display controlling portion 21d, a recording controlling portion 21e, an image judging portion 21f, the voice judging portion 21h and the like.

The image pickup controlling portion 21a is a circuit portion or program software configured to control the image pickup portion 11 to acquire data for displaying a live view image and execute an image pickup operation of acquiring still image data or movie image data in response to a predetermined operation.

The operation judging portion 21b is a circuit portion or program software configured to, in response to an input from the operation portion 13, judge an inputted operation instruction signal. In response to a result of the judgment by the operation judging portion 21b, the image processing controlling portion 21 executes control of a corresponding component unit.

The communication controlling portion 21c is a circuit portion or program software configured to control the apparatus communication portion 12 and the network communication portion 23. In response to an instruction signal from the operation portion 13 or the like, the communication controlling portion 21c performs communication-related control. For example, the image processing controlling portion 21 makes a selection about whether communication is to be performed between terminal apparatuses or communication with the file server 30 is to be performed via the network 40 and controls the selected communication means to perform corresponding various kinds of communication controls.

The display controlling portion 21d is a circuit portion or program software configured to control the display portion 15. In response to an instruction signal from the operation portion 13 or the like, the display controlling portion 21d performs display-related control, for example, performs control to select or switch display content to be displayed by the display panel of the display portion 15.

The recording controlling portion 21e is a circuit portion or program software configured to control the recording portion 16. In response to an instruction signal from the operation portion 13 or the like, the recording controlling portion 21e performs recording-related control, for example, performs control to convert various kinds of information to be recorded to the recording portion 16 to a predetermined data format and record the various kinds of information to a predetermined area of a predetermined storage medium (not shown).

The recording controlling portion 21e has a general order associating portion. The general order associating portion is a component portion configured to play a role of associating information included in general order information created by a doctor or an order information creating portion 31b of the file server 30 with image data acquired by the image pickup portion 11 as medical metadata or general metadata (accompanying information) and handing over the medical metadata or the general metadata to the recording portion 16.

Note that information included in the medical metadata recorded to the recording portion 16 further includes, in addition to the various kinds of information enumerated in the above description, for example, information about communication (communication information), patient information (target information), information about a doctor, information about an order by the doctor (order information and request information), information about treatment and examination of an affected part (condition information), information about an apparatus (apparatus identification information (such as a GS1 Code, a JAN Code, and apparatus serial number) and the like), color chart information, measure (measuring) information, information about apparatus posture and position, approval information as a medical image or a medical reference image and information about whether real or false, and other various kinds of information.

The image judging portion 21f is a circuit portion or program software configured to perform judgment processing for various kinds of information acquired by analyzing, based on image data acquired by the image pickup portion 11, image data transferred from another terminal apparatus or the like and inputted, each piece of image data, for example, judgment processing for light source information about a photographing environment, information about a distance to an object, object (for example, face area) information and the like.

The voice judging portion 21h is a component portion configured to perform predetermined judgment processing based on voice data acquired by the sound collecting portion 24. Therefore, the voice judging portion 21h has processing circuits such as a name judging portion and a response judging portion. Here, for example, the name judging portion detects human voice in voice data acquired by the sound collecting portion 24 and, if human voice is detected, judges whether the human voice is data giving a name. Similarly, for example, the response judging portion detects human voice in voice data acquired by the sound collecting portion 24 and, if human voice is detected, judges whether the human voice is data giving a response.

More specifically, for example, at the time of performing photographing of a patient in the medical reference image photographing mode, the patient is called for identification before photographing, for example, immediately before photographing as described above. In that case, the name judgment and the response judgment are performed based on voice data acquired by the sound collecting portion 24.

Next, the main components of the file server 30 in the medical support system 1 of the present embodiment will be described. Note that the file server 30 corresponds, for example, to a file server included in an existing hospital information system (HIS).

As shown in FIG. 6, the file server 30 is configured being provided mainly with a controlling portion 31, an image database 32, an order information database 33 a patient information database 34, a communication portion 35 and the like.

The controlling portion 31 is a control circuit configured to comprehensively control the file server 30. The controlling portion 31 is configured mainly including a patient judging portion 31a, the order information creating portion 31b, a photographing condition information creating portion 31c and the like.

The patient judging portion 31a is a circuit portion or program software configured to, based on patient-related information and the like included in request information or general order information transferred from the information terminal apparatus (10 or 20), perform association with patient information corresponding to the request information or the general order information.

The order information creating portion 31b is a circuit portion or program software configured to, when a doctor accesses the file server 30 to create order information, refer to various kinds of information of the image database 32, the order information database 33, the patient information database 34 and the like to support creation of the order information.

The order information creating portion 31b is a circuit portion or program software configured to create general order information according to request information in response to instruction information from a doctor (see the second use pattern in FIG. 3).

Here, for example, for general order information about image photographing, some format is specified for each affected part. Therefore, at the time of creating general order information, a doctor can create the general order information in a rough form by selecting a desired examination classification (for example, "image photographing examination"), a desired affected part (for example, "face" or "knee") and the like.

Furthermore, in the medical support system 1 of the present embodiment, for example, it is possible to refer to electronic medical record information, examination history information and the like about a target patient in the patient information database 34 and, if an order that is the same as or similar to a currently intended examination or the like (for example, "image photographing examination") exists in a list of orders of examinations performed in the past, reads the information to cause new general order information to be created.

As described above, the order information creating portion 31b is a component portion configured to, when a doctor creates order information (either medical order information or general order information), omit or improve efficiency of input work to support creation of the order information.

The photographing condition information creating portion 31c is a circuit portion or program software configured to, if order information created by the order information creating portion 31b based on an instruction from a doctor is, for example, an order involving image photographing, create photographing condition information suitable for the image photographing instruction.

The photographing condition information creating portion 31c refers to past order information at the time of similar "image photographing examinations" performed in the past, information about results of the examinations (such as acquired and recorded image data and accompanying information of the image data) and the like, based on patient information and the like referred to at the time of creating order information, and creates photographing condition setting information optimal for image photographing corresponding to current order information.

In a normal case, when a doctor creates order information, the doctor only gives a medical action instruction. In the medical support system 1 of the present embodiment, however, the photographing condition information creating portion 31c creates photographing condition information for performing image photographing based on the order information configured only with the medical action instruction, which has been created by the doctor. The photographing condition information is communicated to the information terminal apparatus (10 or 20) for photographing (acquiring) image data in response to created general order information and used at the time of photographing.

The image database 32 is a database portion in which image data is accumulated. The plurality of pieces of image data accumulated in the image database 32 include, in addition to various kinds of image data included in each piece of specific patient information, for example, medical images or medical reference images obtained by photographing an affected part or a symptom of a particular patient and an image including a face for identifying the patient, sample images and the like prepared in advance to be referred to at the time acquiring an image of a particular affected part or a particular symptom.

Here, the medical images or the medical reference images specifically include, for example, image data in which a preoperative or postoperative course is recorded during a medical examination process, and image data in which a state of an affected part during an operation is recorded. Forms of the image data in this case include, in addition to image data recorded by a general image pickup apparatus, X-ray image data, ultrasound image data, endoscopic image data and the like. Among the above pieces of data, the X-ray image data, the ultrasound image data, the endoscopic image data and the like are image data acquired by various kinds of medical-related qualified workers using dedicated apparatuses installed in medical bases such as hospitals in response to doctors' orders (requests) and are medical images approved by the doctors.

Among the plurality of pieces of image data accumulated in the image database 32, each of pieces of image data other than sample images is recorded in a form of being associated with a corresponding piece of medical-related information (such as electronic medical record information and patient information). Furthermore, for each piece of image data, metadata including photographing date and time information and the like, and medical metadata to which various kinds of information is further given based on a patient ID and electronic medical record information are recorded accompanying the piece of image data.

The order information database 33 is a database portion in which information about order information issued by doctors is accumulated. As the information recorded to the order information database 33, there is sample information of order specification sheets set in advance, for example, for predetermined affected parts or predetermined symptoms. In the order specification sheets, for example, a doctor name (a requester name), a patient ID, used apparatus information and photographing condition information are written.

In general, in order for a doctor to perform an examination and the like for a particular patient, the doctor is required to issue order information appropriate for an affected part or a symptom for each target patient of the examination, at the time of requesting acquisition of image data to each medical department.

In this case, there is an advantage that, since the order information database 33 is provided, the doctor does not have to create the order information to be newly created, from scratch.

That is, the doctor can refer to an order specification sheet (a sample) corresponding to an affected part or a symptom of a currently targeted patient among the plurality of order specification sheets (samples) recorded in the order information database 33, and, therefore, it becomes possible to create an order specification sheet optimal for each target patient according to a symptom, an affected part or the like of the target patient.

The patient information database 34 is a database portion in which patient information, for example, patient IDs and electronic medical record information are accumulated.

The communication portion 35 is a circuit portion or program software configured to mutually perform transmission/reception of various kinds of data files with the plurality of information terminal apparatuses (10 and 20) via the network 40. The communication portion 35 is controlled by a communication controlling portion (not shown) included in the controlling portion 31 so that predetermined communication is executed.

Operation of the medical support system 1 of the present embodiment configured as described above will be described below. Note that the operation described below basically assumes the operation of the "second pattern" or the "third pattern" among the respective use patterns described above.

Figure 7:
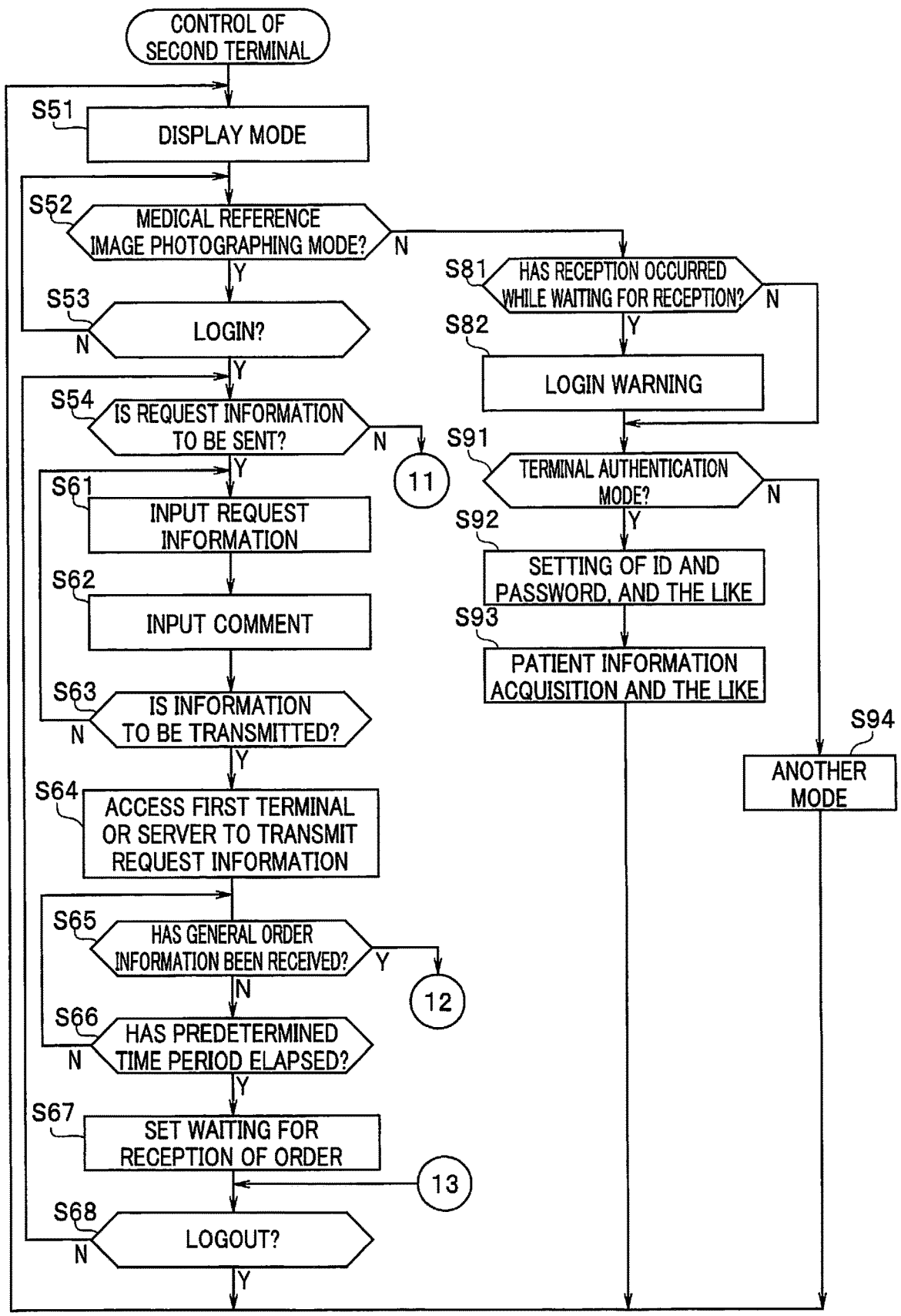
FIG. 7 is a flowchart (a first half) showing operation of a second terminal among information terminal apparatuses in the medical support system of the one embodiment of the present invention.
Figure 8:
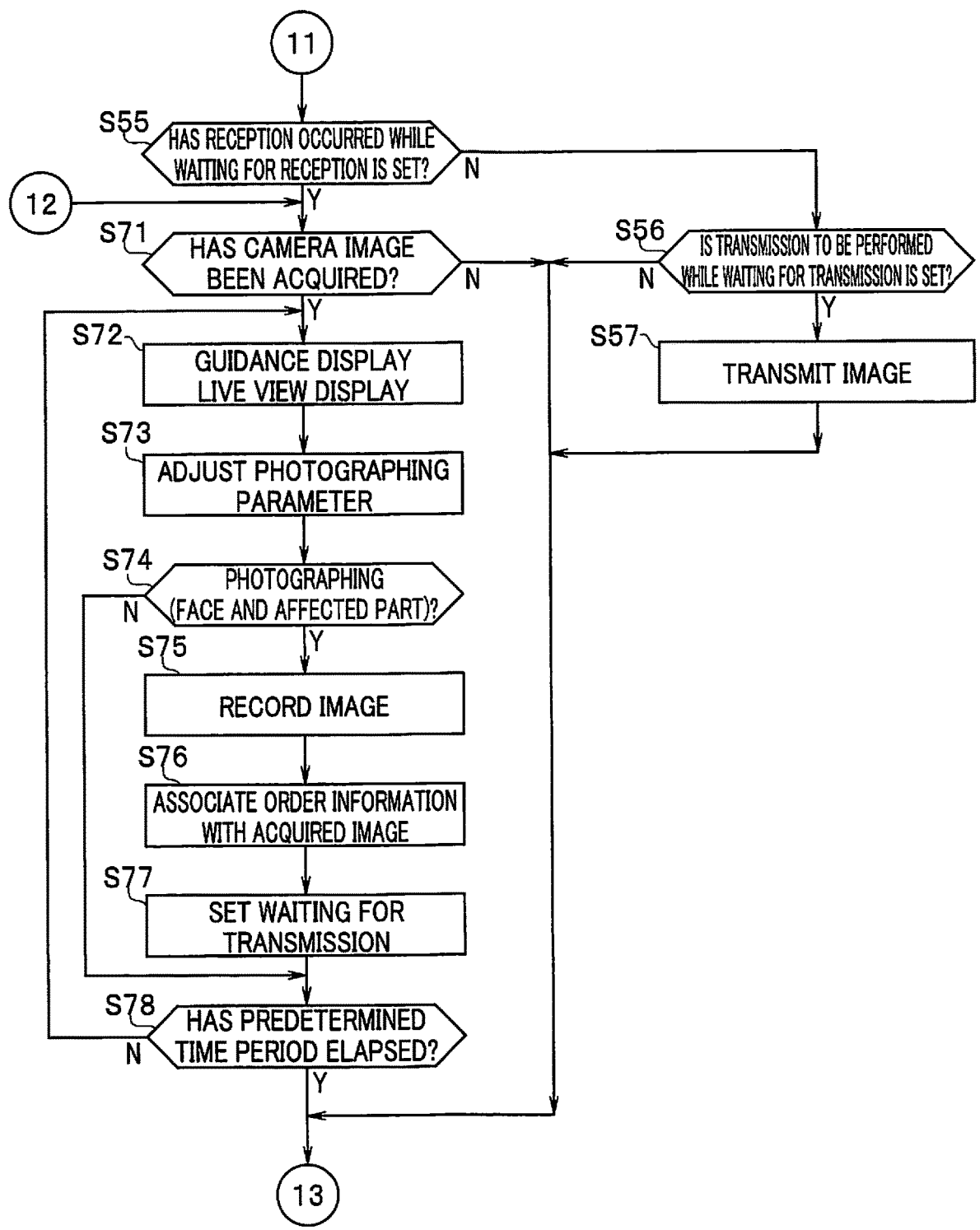
FIG. 8 is the flowchart (a latter half) showing the operation of the second terminal among the information terminal apparatuses in the medical support system of the one embodiment of the present invention.

First, operation of the second terminal 20 among the information terminal apparatuses in the medical support system 1 of the present embodiment will be described. FIGS. 7 and 8 are flowcharts showing the operation of the second terminal 20 among the information terminal apparatuses in the medical support system of the present embodiment.

In the medical support system 1 of the present embodiment, the second terminal 20 is assumed to be, for example, an information terminal apparatus used by a person other than a doctor, for example, a patient's family member as described above.

First, it is assumed that the second terminal 20 has been powered up and activated to be in a usable state.

In this state, first, the image processing controlling portion 21 of the second terminal 20 controls the display controlling portion 21d or the like to display an operation mode that is currently set, on the display screen of the display portion 15 at step S51 in FIG. 7. For example, as operation modes displayed here, that is, operation modes that can be executed by the second terminal 20, there are various kinds of operation modes executed by the "medical reference image acquisition application" described above, for example, the request information creation mode, the request information transmission mode, the general order information reception mode, the medical reference image photographing mode and the medical reference image transfer mode, in addition to a normal photographing mode, a reproduction mode, a various-kinds-of-settings mode and a mode for communication with other apparatuses and the like. Note that, in a normal case, an operation mode set by default immediately after the second terminal 20 is powered up is the photographing mode.

Then, at step S52, the image processing controlling portion 21 confirms the operation mode currently set and confirms whether the operation mode currently set is the medical reference image photographing mode or not. If the operation mode currently set is the medical reference image photographing mode, the image processing controlling portion 21 proceeds to processing of next step S53. If the operation mode currently set is an operation mode other than the medical reference image photographing mode, the image processing controlling portion 21 proceeds to processing of step S81.

At step S53, the image processing controlling portion 21 executes predetermined login processing. As the login processing, login processing for direct connection from the second terminal 20 to the first terminal 10 of a doctor or login processing for connecting to the file server 30 via the network 40 is assumed. Note that, for example, input of an ID issued from the doctor or a hospital-side system in advance and a password are required for the login processing. As input means in this case, for example, direct input by operating the touch panel or image recognition input using a barcode or a QR code (registered trademark) is possible.

The login processing here may be login processing for executing a series of operations in the medical reference image photographing mode using the second terminal 20. That is, in order to execute a certain particular operation mode, predetermined login processing is to be performed at the time of executing the operation mode. By providing such login processing for an operation mode, it is possible to enable only a person whose identification has been verified to cause the series of operations in the medical reference image photographing mode to be executed, using a terminal authenticated by the doctor or the hospital in advance.

When the login processing is completed here, the image processing controlling portion 21 proceeds to processing of next step S54. If the login processing is not completed here, the image processing controlling portion 21 returns to the processing of step S52 described above.

Note that an operation procedure for the login processing performed by the processing of step S53 described above is, for example, an operation of inputting information (particular information such as a patient registration card number) issued from the doctor, the hospital or the like to a particular person (a patient or the patient's family member). More specifically, an operation of touching a numeric keypad displayed on the display screen is performed, for example, using the touch panel as an input operation member. An operation of reading, for example, code information issued from the doctor, the hospital or the like to the particular person (the patient or the patient's family member) (a code including particular information, such as a patient registration card number, in a form of a barcode, or a QR code (registered trademark) using a code reading application of the second terminal 20 is also possible.

At step S54, the image processing controlling portion 21 confirms whether request information is to be sent or not. Here, if request information has not been sent yet and is to be issued, the image processing controlling portion 21 proceeds to processing of next step S61. If request information has already been sent, or if request information is not to be issued, the image processing controlling portion 21 proceeds to processing of step S55 in FIG. 8 (see circled reference numeral 11 in FIGS. 7 and 8).

If the image processing controlling portion 21 proceeds to step S61 assuming that request information is to be issued by the processing of step S54 described above, the image processing controlling portion 21 switches the operation mode to the request information creation mode and accepts processing for inputting basic information in the request information appropriately inputted from a user at step S61. Then, at step S62, the image processing controlling portion 21 accepts processing for inputting comment information in the request information appropriately inputted from the user.

The request information inputted at steps S61 and S62 described above is, for example, information attached as comments in addition to the basic information identifying the patient, and it is assumed to provide information for consulting a current state of a disease and the like including chief complaint, from the patient side to the doctor.

Whether or not the doctor who has received such request information issues general order information in response to the request information depends on the doctor's judgment. Therefore, there may be a possibility that, even if request information is sent to the doctor from the patient side, a response from the doctor, for example, sending of general order information about an image, or the like is not performed. If the doctor considers that an image and the like of the patient are not necessary, such general order information is not sent.

Therefore, the request information created at steps S61 and S62 described above and sent to the doctor from the patient side as described later is considered much as consultation information to the doctor.

When the request information input processing ends in this way, the image processing controlling portion 21 proceeds to processing of next step S63.

At step S63, the image processing controlling portion 21 confirms whether processing for transmitting the created request information is to be executed or not. Here, if the request information transmission processing is to be executed, the image processing controlling portion 21 proceeds to processing of next step S64. If the request information transmission processing is not to be executed, for example, if additional input to the request information is to be performed, the image processing controlling portion 21 returns to the processing of step S61 and repeats the subsequent processing.

At step S64, the image processing controlling portion 21 switches the operation mode to the request information transmission mode. Then, the communication controlling portion 21c of the image processing controlling portion 21 controls the apparatus communication portion 12 or the network communication portion 23 to access the doctor's first terminal 10 or the file server 30 of a hospital system, and executes the request information transmission processing. After that, the image processing controlling portion 21 switches the operation mode to the general order information reception mode and enters a reception waiting state.

Next, at step S65, the image processing controlling portion 21 confirms whether general order information has been received or not. The general order information is information sent from the doctor's first terminal 10 or the file server 30 of the hospital system to the second terminal 20.

If the general order information has been received, the image processing controlling portion 21 proceeds to processing of step S71 in FIG. 8 (see circled reference numeral 12 in FIGS. 7 and 8). If the general order information has not been received, the image processing controlling portion 21 proceeds to processing of step S66.

At step S66, the image processing controlling portion 21 refers to the clock portion 22 to confirm whether a predetermined time period has elapsed or not. If the predetermined time period has elapsed, the image processing controlling portion 21 proceeds to processing of next step S67. If the predetermined time period has not elapsed, the image processing controlling portion 21 returns to the processing of step S65 described above and repeats the confirmation of reception.

If it is confirmed by the processing of step S66 described above that the predetermined time period has elapsed, and the image processing controlling portion 21 proceeds to processing of step S67, then the image processing controlling portion 21 sets an order reception waiting mode at step S67. The order reception waiting mode is a reception waiting mode for receiving general order information as a response to the transmitted request information. In the second terminal 20, by setting the reception waiting mode, it is possible to cause other desired work processing to be executed in parallel while being always in the reception waiting state. When setting of the order reception waiting mode is completed, the image processing controlling portion 21 proceeds to processing of next step S68.

At step S68, the image processing controlling portion 21 confirms whether logout processing is to be performed or not. If an instruction signal instructing logout processing is confirmed, the image processing controlling portion 21 proceeds to the processing of step S51 described above after executing predetermined logout processing. If the instruction signal instructing logout processing is not confirmed, the image processing controlling portion 21 returns to the processing of step S54 described above and repeats the subsequent processing.

On the other hand, if the operation mode currently set is confirmed as an operation mode other than the medical reference image photographing mode in the processing of step S52 described above, and the image processing controlling portion 21 proceeds to the processing of step S81, then the image processing controlling portion 21 confirms at step S81 whether reception of general order information has been performed or not. In a case where reception of general order information is confirmed here, the image processing controlling portion 21 proceeds to processing of next step S82. In a case where reception of general order information is not confirmed, the image processing controlling portion 21 proceeds to processing of step S91. Note that the case where reception of general order information is confirmed is the case where the order reception waiting mode is set by the processing of step S67 described above.

At step S82, the display controlling portion 21d of the image processing controlling portion 21 controls the display portion 15 to display a predetermined login warning on the display screen of the display portion 15. The login warning is display that prompts the user to perform a login operation for logging in the first terminal 10 or the file server 30 to acquire the received general order information.

Note that though description is made using the expression of "general order information is received" in the above description of step S81, a substantial part of the information is not actually received by the processing of step S81. It is meant that, at the point of time of step S81, for example, a mere notification to the effect that general order information has been sent from the doctor or the file server 30 to the second terminal 20 has been received. Therefore, in order to receive the substance of the general order information, the login processing is performed at step S82 described above.

After appropriately performing a login operation, the user of the second terminal 20 performs a predetermined operation to receive the general order information. Note that, as described above, the order reception waiting mode is executed in parallel with other operation processing. Therefore, after the general order information reception processing ends, the user can return to the other operation processing.

That is, when the operation mode currently set is confirmed as a mode other than the medical reference image photographing mode in the processing of step S52 described above, the processing branches to the processing of step S81, and, therefore, another operation following the processing of step S82 described above is executed by transition to processing of step S91.

That is, at step S91, the image processing controlling portion 21 confirms whether the operation mode currently set is a terminal authentication mode or not. Here, the terminal authentication mode is an operation mode for performing a registration procedure and the like for enabling the second terminal 20 to be used in the medical support system 1.

Note that the registration procedure in the terminal authentication mode is an operation required to be performed once first at the time of using an information terminal apparatus (the second terminal 20) in the medical support system 1. At the time of using a registered information terminal apparatus second time and subsequently, the information terminal apparatus can be used in the medical support system 1 by using an ID and a password set and acquired by the first registration procedure.

Here, if it is confirmed that the mode is set to the terminal authentication mode, the image processing controlling portion 21 proceeds to processing of next step S92. If the mode is not the terminal authentication mode, the image processing controlling portion 21 proceeds to processing of step S94.

Then, at step S94, the image processing controlling portion 21 executes processing in another operation mode. Note that, as the other mode, a telephone communication mode, a mail transmission/reception mode or the like is conceivable in the case of an image-pickup-function-equipped communication apparatus (a device such as a smartphone). In the case of a communication-function-equipped image pickup apparatus (a device such as a digital camera), a normal photographing mode, a reproduction mode, a menu mode (a setting mode) or the like is conceivable.

However, since the other operation modes are not directly related to the present invention, details of the operation modes are not described or shown. Therefore, as for the subsequent processing, it is assumed that the image processing controlling portion 21 returns to the processing of step S51 described above.

As described above, if it is confirmed that the terminal authentication mode is set, and the image processing controlling portion 21 proceeds to the processing of step S92, then the image processing controlling portion 21 executes processing related to a registration procedure required for terminal authentication, such as ID setting processing and password setting processing at step S92. After that, the image processing controlling portion 21 proceeds to processing of step S93.

At step S93, the operation judging portion 21b of the image processing controlling portion 21 executes processing for acquiring patient information and the like about the target patient from the file server 30, and the like in response to an operation instruction signal inputted from the operation portion 13 or the touch panel 14. When the necessary processing ends, the image processing controlling portion 21 waits for an end instruction signal, returns to the processing of step S51 described above and repeats the subsequent processing.

On the other hand, if request information is not to be sent at step S54 described above, and the image processing controlling portion 21 proceeds to step S55, then the image processing controlling portion 21 confirms at step S55 whether reception of general order information has been performed or not. If reception of general order information is confirmed here, the image processing controlling portion 21 proceeds to processing of next step S71. In this case, since the login state is maintained, the substance of the general order information has been received.

If reception of general order information is not confirmed, the image processing controlling portion 21 proceeds to processing of step S56. Here, the case where the image processing controlling portion 21 proceeds to the processing of step S56 is a situation shown below. That is, the situation is a situation in which it is confirmed by the processing of step S52 described above that the mode is the medical reference image photographing mode, login is completed by the processing of step S53 described above, it is confirmed by the processing of step S54 described above that request information is not to be sent, and it is confirmed by the processing of step S55 described above that reception of general order information has not been performed. For such a situation, for example, a case is conceivable wherein the series of operation in the medical reference image photographing mode (transmission of request information, reception of general order information and photographing in the medical reference image photographing mode) has been already performed, and image data as a desired medical reference image has been already acquired. In such a case, the image processing controlling portion 21 proceeds to the processing of step S56, and operation processing in the medical reference image transfer mode is executed (to be described later).

Note that the case where reception of general order information is confirmed is the case where the order reception waiting mode has been set by the processing of step S67 described above similarly to the processing of step S81 described above.

When reception of general order information is confirmed, the image processing controlling portion 21 of the second terminal 20 switches the operation mode to the medical reference image photographing mode. The user (the patient's family member) of the second terminal 20 executes a predetermined photographing operation according to the received general order information using the second terminal 20.

At step S71, the image processing controlling portion 21 confirms whether or not predetermined photographing processing has been executed, and image data has been acquired. If acquisition of image data is confirmed, the image processing controlling portion 21 proceeds to processing of step S72. If acquisition of image data is not confirmed (in a case where photographing has not been performed yet), the image processing controlling portion 21 returns to the processing of step S68 in FIG. 7 (see circled reference numeral 13 in FIGS. 7 and 8).

When acquisition of image data is confirmed, the image processing controlling portion 21 displays guidance information (for example, a photographing procedure and display of information) and comment information included in the received general order information and performs live view display for sequentially displaying image data acquired by the image pickup portion 11 at step S72. In this case, the general order information and the live view may be displayed in chronological order, may be overlappedly displayed or may be switchedly displayed by appropriately operating an operation member.

Then, at step S73, the image processing controlling portion 21 executes processing for adjusting photographing parameters and the like in the second terminal 20 in consideration of information such as photographing conditions included in the received general order information.

Next, at step S74, the image processing controlling portion 21 confirms whether photographing (for example, a face image and an affected part image of the patient) according to the general order information has been performed or not.

Here, for example, a face image of the patient is acquired together with a desired affected part image, and this is for the purpose of confirming whether or not the desired affected part image photographed at the same time is an image of the patient himself/herself. The user is notified that such an identification image is simultaneously acquired at the time of acquiring a medical reference image by the processing of step S72 described above or the like, for example, based on various kinds of instructions included in the guidance information or the like included in the general order information. Since the user performs photographing according to the guidance information, the user can acquire the identification image as described above together with a desired affected part image without failing to acquire the identification image.

When confirming that photographing according to the general order information has been performed, by the processing of step S74 described above, the image processing controlling portion 21 proceeds to processing of next step S75. When confirming that photographing according to the general order information has not been performed, the image processing controlling portion 21 proceeds to processing of step S78.

At step S75, the recording controlling portion 21e of the image processing controlling portion 21 executes processing for recording the acquired image data.

Then, at step S76, the recording controlling portion 21e of the image processing controlling portion 21 executes association processing for associating various kinds of information included in the general order information with the acquired image data.

Next, at step S77, the image processing controlling portion 21 sets an image transmission waiting mode for transmitting image data of a medical reference image. The image transmission waiting mode is a transmission waiting mode for transmitting image data (a medical reference image) photographed according to received general order information. In the second terminal 20, by setting the transmission waiting mode, it is possible to cause other desired work processing to be executed in parallel while being always in a transmission waiting state. When setting of the image transmission waiting mode is completed, the image processing controlling portion 21 proceeds to processing of next step S78.

Note that, as a situation in which the image transmission waiting mode is set, a case is conceivable where the second terminal 20 is in an environment in which communication with the first terminal 10 or the file server 30 is impossible. In such a case, the image transmission waiting mode is set, and, at the time of having moved to a place in a good communication environment, communication can be secured, and transmission can be performed.

At step S78, the image processing controlling portion 21 refers to the clock portion 22 to confirm whether a predetermined time period has elapsed or not. If the predetermined time period has elapsed, the image processing controlling portion 21 proceeds to processing of step S68 in FIG. 7 (see circled reference numeral 13 in FIGS. 7 and 8). If the predetermined time period has not elapsed, the image processing controlling portion 21 returns to the processing of step S72 described above and repeats the subsequent processing.

If reception of general order information has not been performed at step S55 described above, and the image processing controlling portion 21 proceeds to the processing of step S56, then the image processing controlling portion 21 confirms at step S56 whether processing for transmitting the image data of the acquired medical reference image has been executed or not. Note that it is about whether execution of the transmission processing is possible or not that is confirmed here. If execution of the transmission processing is possible here, the image processing controlling portion 21 proceeds to processing of next step S57.

Then, at step S57, the image processing controlling portion 21 executes predetermined image transmission processing after switching the operation mode to the medical reference image transfer mode. After that, the image processing controlling portion 21 returns to the processing of step S68 in FIG. 7 (see circled reference numeral 13 in FIGS. 7 and 8).

On the other hand, if that execution of the transmission processing is impossible in the processing of step S56 described above is confirmed, the image processing controlling portion 21 also returns to the processing of step S68 in FIG. 7 (see circled reference numeral 13 in FIGS. 7 and 8).

Figure 9:
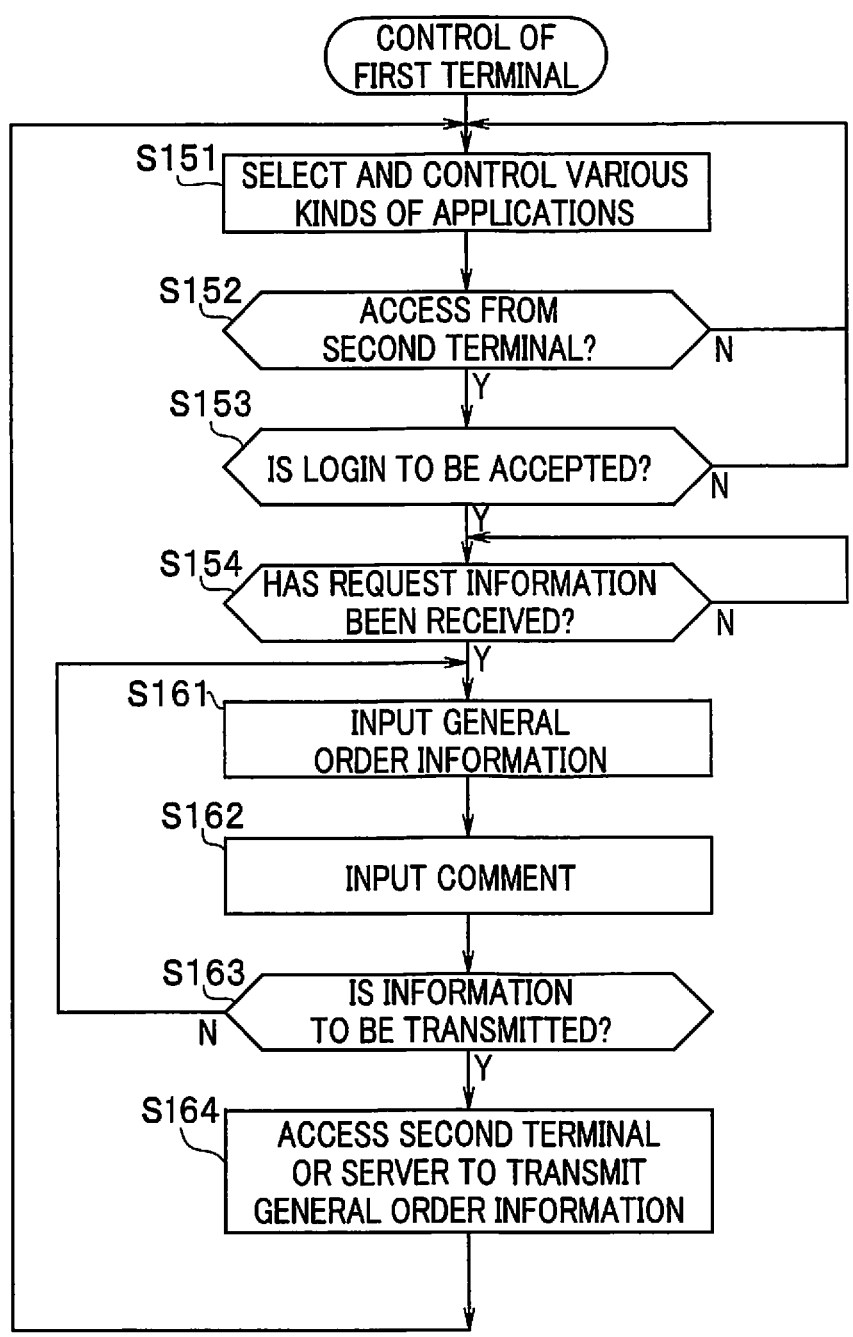
FIG. 9 is the flowchart showing operation of a first terminal among the information terminal apparatuses in the medical support system of the one embodiment of the present invention.

Next, operation of the first terminal 10 among the information terminal apparatuses in the medical support system 1 of the present embodiment will be described. FIG. 9 is a flowchart showing the operation of the first terminal 10 among the information terminal apparatuses in the medical support system of the present embodiment.

Description will be made on the assumption that, in the medical support system 1 of the present embodiment, the medical support system 1 is an information terminal apparatus (more specifically, a tablet PC) used, for example, by a doctor as described above.

First, the image processing controlling portion 21 of the first terminal 10 controls the display controlling portion 21d or the like to display a plurality of icons indicating various kinds of pieces of executable application software on the display screen of the display portion 15 at step S151 in FIG. 9 so that the image processing controlling portion 21 can respond to work using various applications.

For example, it is possible to perform telephone contact, e-mailing or chat contact with clerical workers, medical workers and involved persons inside and outside a medical facility. By the terminal, it is possible to select not only schedule management or reading of patient information but also search for various kinds of information from among icons. It is possible to easily create a work record and the like making full use of the applications. Since a dictation application and the like may be used for creation of a document nowadays, the terminal is compatible with such a technique.

It is preferred that the terminal enables not only the above state but also access from an external apparatus. Consequently, the doctor can respond to an emergency patient by the terminal or can respond to inquiries from other medical workers. Here, description is made by an expression that one of the applications that executes the processing of step S151 is a waiting function described below though the function is expressed in a form of following step S151. The object of the present invention can be achieved by such design that applications operate in parallel.

At step S152, the image processing controlling portion 21 confirms whether or not there is access, for example, from the second terminal 20. Though the applications at S151 include various functions other than the access confirmation, description is simplified here. Since a characteristic part of the present invention can be described by S152 and subsequent steps, description will be made below in a form of especially mentioning the characteristic part of the present invention.

When access from the second terminal 20 is confirmed at step S152, the image processing controlling portion 21 proceeds to processing of next step S153. If access from the second terminal 20 is not confirmed, the image processing controlling portion 21 returns to the processing of step S151.

Note that when being in a waiting state, the first terminal 10 can accept other various kinds of input instructions and the like even if access from the second terminal 20 is not confirmed. However, operations corresponding to such other input instructions and the like are not directly related to the present invention. Therefore, if access from the second terminal 20 is not confirmed by the processing of step S152, the image processing controlling portion 21 returns to the processing of step S151 for convenience, without describing the operations corresponding to the other input instructions and the like.

Then, at step S153, the image processing controlling portion 21 confirms whether login procedure processing (the login processing at step S53 in FIG. 7) from the second terminal 20 is authorized or not, that is, whether the login is to be accepted or not. If the login is to be accepted, the image processing controlling portion 21 proceeds to processing of next step S154. If the login is not to be accepted, the image processing controlling portion 21 returns to the processing of step S151. Here, the case where the login is not to be accepted is a case where information included in the login procedure, for example, a login ID or a password does not match, or the like.

When the login is accepted, and the image processing controlling portion 21 proceeds to processing of step S154, the image processing controlling portion 21 waits for reception of information following the login. Since there may be abrupt communication disconnection or arrival of irregular information, it may be designed to wait for a predetermined time period, or some warning may be issued. However, a simplified expression is adopted here.

The image processing controlling portion 21 switches to a request information reception mode for receiving request information. Then, the image processing controlling portion 21 receives transmitted request information and confirms whether the request information has been received or not (processing corresponding to the request information transmission by the processing of step S54 in FIG. 7). Here, the image processing controlling portion 21 repeats the reception confirmation processing until request information is received. If request information is received, the image processing controlling portion 21 proceeds to processing of next step S161. Note that when a predetermined time period elapses without receiving request information, the image processing controlling portion 21 may exit the loop and return to the processing of step S151, though this is not shown in the flowchart of FIG. 9.

Next, at step S161, the image processing controlling portion 21 switches to the general order information creation mode and waits for a user's input instruction. A user appropriately inputs corresponding general order information according to the request information received by the processing of step S154 described above.

Then, at step S162, the image processing controlling portion 21 accepts comment information input processing for inputting arbitrary comments to be included in the general order information appropriately inputted by the user.

The general order information inputted at steps S161 and S162 described above is, for example, in addition to basic information for identifying a patient, information given as comments; and the information is information issued by the doctor in response to request information from the patient's family member, and various kinds of information including image photographing instruction information and the like.

When the general order information input processing ends in this way, the image processing controlling portion 21 proceeds to processing of next step S163.

At step S163, the image processing controlling portion 21 confirms whether or not to execute processing for transmitting the created general order information. If the general order information transmission processing is to be executed, the image processing controlling portion 21 proceeds to processing of next step S164. If the general order information transmission processing is not to be executed, for example, if additional input to the created general order information is to be performed, the image processing controlling portion 21 returns to the processing of step S161 and repeats the subsequent processing.

At step S164, the image processing controlling portion 21 switches the operation mode to the general order information transmission mode. Then, the communication controlling portion 21c of the image processing controlling portion 21 controls the apparatus communication portion 12 or the network communication portion 23 to access the second terminal 20 of the patient's family member or the file server 30 of the hospital system and execute the processing for transmitting the created general order information. After that, the image processing controlling portion 21 switches the operation mode to a normal waiting state.

Note that the first terminal 10 can operate in various operation modes other than the operation modes described above. However, since the other operation modes of the first terminal 10 are not directly related to the present invention, description of the operation modes will be omitted.

As for the flowchart shown in FIG. 9 also, only parts required to describe the operation of the present invention are shown, and parts that are not directly related to the present invention are not shown or described. As for operations of the parts that are not described, it is assumed that operations similar to operations of a conventional general information terminal apparatus (a tablet PC is assumed in the present embodiment) can be realized.

Furthermore, in the first terminal 10, it is also similar to a conventional information terminal apparatus of a same type that it is possible to realize various operations depending on installed application software.

Figure 10:
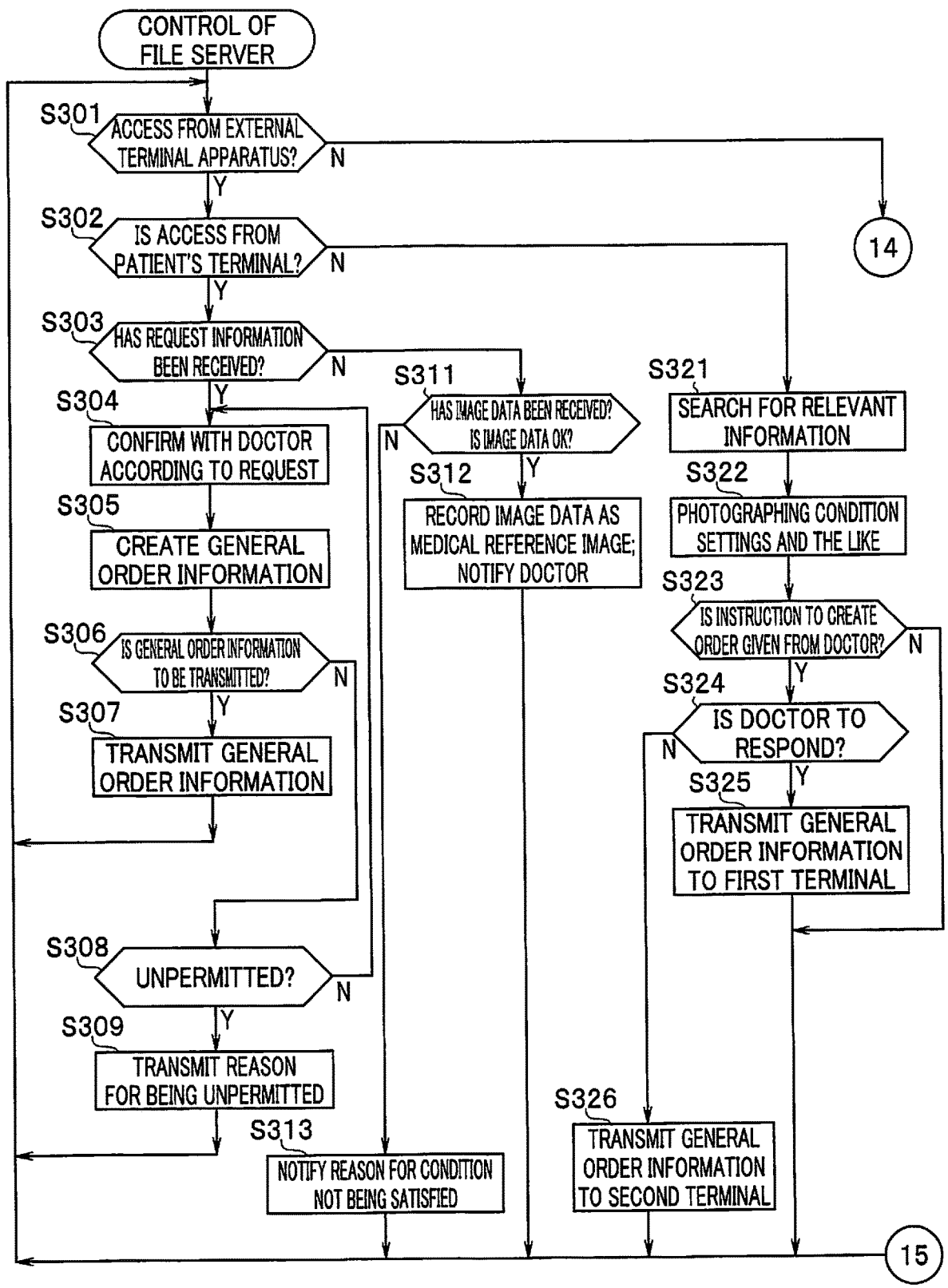
FIG. 10 is a flowchart (a first half) showing operation of the file server in the medical support system of the one embodiment of the present invention.
Figure 11:
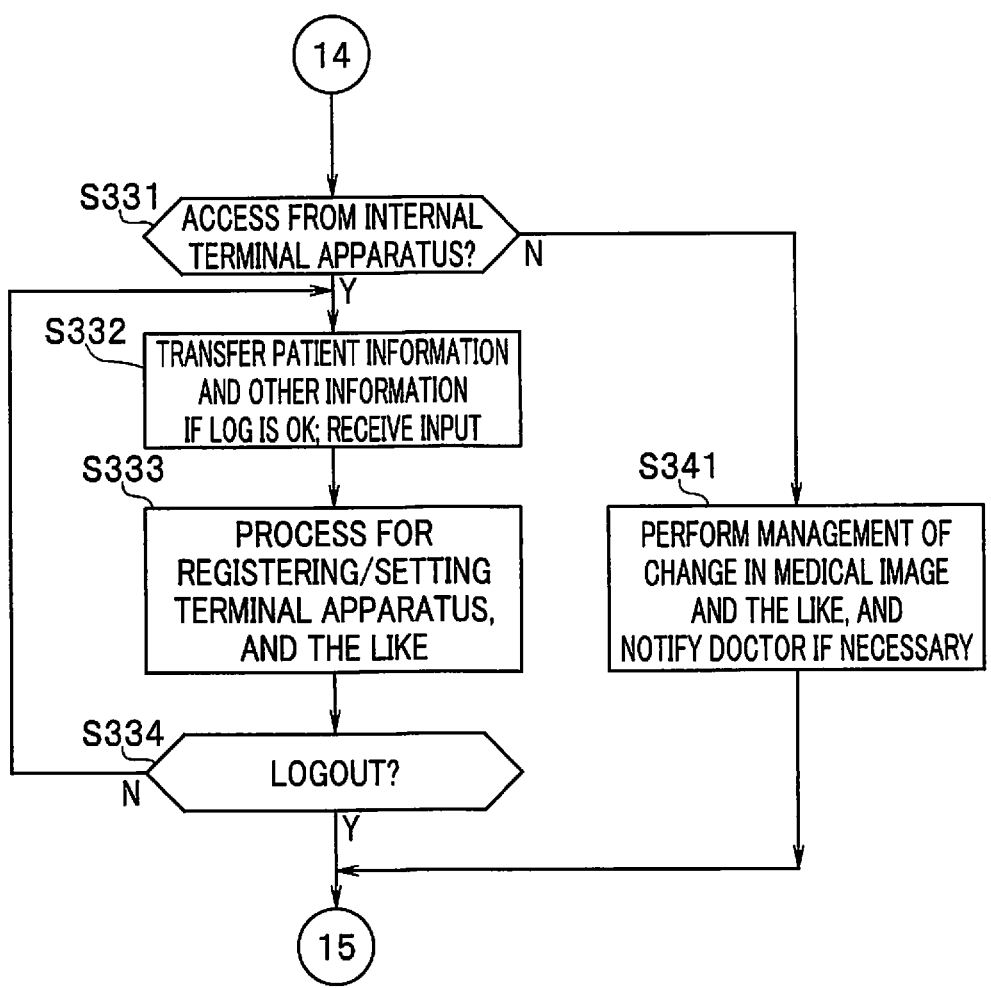
FIG. 11 is the flowchart (a latter half) showing the operation of the file server in the medical support system of the one embodiment of the present invention.

Next, operation of the file server 30 in the medical support system 1 of the present embodiment will be described. FIGS. 10 and 11 are flowcharts showing the operation of the file server in the medical support system of the present embodiment.

First, it is assumed that the file server 30 is in an activated state and is in a waiting state of waiting for access from another apparatus such as an external information terminal apparatus or an internal terminal apparatus.

Here, the external information terminal apparatus refers to the first terminal 10, the second terminal 20 or the like. Note that, in FIG. 10, the first terminal 10, the second terminal 20 or the like is simply expressed as an external terminal apparatus. The internal terminal apparatus refers to a PC or the like installed in the reception department or a medical examination room in the medical facility (not shown). Therefore, the file server 30 allows access not only from the external information terminal apparatuses (10, 20 and the like) but also from the internal terminal apparatuses.

When the file server 30 is in this state, the communication portion 35 of the controlling portion 31 confirms whether there is access from an external information terminal apparatus (10, 20 or the like) at step S301 in FIG. 10. If access from an external information terminal apparatus (10, 20 or the like) is confirmed, the communication portion 35 proceeds to processing of next step S302. If access from an apparatus other than the external information terminal apparatuses (10, 20 and the like) is confirmed, the communication portion 35 proceeds to processing of step S331 in FIG. 11 (see circled reference numeral 14 in FIGS. 10 and 11).

At step S302, the communication portion 35 of the controlling portion 31 confirms whether the access is from the second terminal 20. If access from the second terminal 20 is confirmed, the communication portion 35 proceeds to processing of next step S303 after executing predetermined login processing. If access from an apparatus other than the second terminal 20 (that is, the first terminal 10) is confirmed, the communication portion 35 proceeds to processing of step S321 after executing predetermined login processing.

At step S303, the controlling portion 31 confirms whether request information from the second terminal 20 has been received or not. If it is confirmed that request information has been received, the controlling portion 31 proceeds to processing of step S304. If request information has not been received, the controlling portion 31 proceeds to processing of step S311.

At step S304, the controlling portion 31 confirms with a corresponding doctor according to the received request information. The processing performed here corresponds to, for example, processing for transferring the received request information to the first terminal 10 of the corresponding doctor. The doctor who receives the request information performs a predetermined operation using his/her own first terminal 10 though it is not shown.

Next, at step S305, the controlling portion 31 creates general order information based on instruction information received from the doctor by the processing of step S304 described above.

Then, at step S306, the controlling portion 31 confirms about a transmission instruction signal indicating whether the general order information created by the processing of step S305 described above is to be transmitted to the second terminal 20, which is a sender of the received request information. The transmission instruction signal is an instruction signal issued from the doctor.

If the general order information transmission instruction signal is confirmed here, the controlling portion 31 proceeds to processing of next step S307. If the general order information transmission instruction signal is not confirmed, the communication portion 35 proceeds to processing of step S308.

At step S307, the controlling portion 31 executes transmission processing for transmitting the general order information created by the processing of step S305 described above to the second terminal 20, which is the sender of the received request information. After that, the controlling portion 31 returns to the processing of step S301 and repeats the subsequent processing. That is, the file server 30 enters the state of waiting for access from an external apparatus.

On the other hand, if the general order information transmission instruction signal is not confirmed by the processing of step S306 described above, and the controlling portion 31 proceeds to the processing of step S308, then the controlling portion 31 confirms information about whether transmission can be permitted or not. The information about whether transmission can be permitted or not is information that can be checked, for example, by whether a checkmark is put on the permission display 10b (see FIGS. 2 and 3) included in the general order information created by the processing of step S305 described above.

If information to the effect that transmission is permitted is confirmed, the controlling portion 31 returns to the processing of step S304 described above and repeats the subsequent processing. If the information to the effect that transmission is permitted is not confirmed, that is, if there is information to the effect that transmission is not permitted, the controlling portion 31 proceeds to processing of step S309.

At step S309, the controlling portion 31 transmits information including a reason why transmission is not permitted to the second terminal 20, which is the sender of the received request information. After that, the controlling portion 31 returns to the processing of step S301 and repeats the subsequent processing. That is, the file server 30 enters the state of waiting for access from an external apparatus.

On the other hand, if access from an apparatus other than the external information terminal apparatuses (10, 20 and the like) is confirmed by the processing of step S301 described above, and the controlling portion 31 proceeds to the processing of step S331 in FIG. 11, then the controlling portion 31 confirms whether or not there is access from an internal terminal apparatus (not shown; for example, an internal terminal apparatus (not shown) such as a PC installed in the reception department, or a medical examination room in the medical facility) at step S331. If access from an internal terminal apparatus is confirmed, the controlling portion 31 proceeds to processing of next step S332. If access from an internal terminal apparatus is not confirmed, the controlling portion 31 proceeds to processing of step S341.

At step S332, the controlling portion 31 executes predetermined login procedure processing. In response to the execution, the internal terminal apparatus (not shown) performs predetermined login procedure processing. When login to the file server 30 is completed (in a case where login is OK), the controlling portion 31 transfers predetermined information to the internal terminal apparatus in response to a request from the internal terminal apparatus. In response to the transfer, the internal terminal apparatus displays the predetermined information on a display portion (not shown). The controlling portion 31 performs information recording processing in response to input of information from the internal terminal apparatus (for example, input for updating electronic medical record). After that, the controlling portion 31 proceeds to processing of step S333.

Note that if the internal terminal apparatus cannot log in the file server 30, the file server 30 cancels the subsequent processing, returns to the processing of step S301 described above and enters the waiting state, though it is not shown.

At step S333, in response to an operation instruction from the internal terminal apparatus, the controlling portion 31 executes processing for registering/setting an information terminal apparatus (10, 20), and the like.

Then, at step S334, the controlling portion 31 confirms a logout instruction from the access source apparatus. If a logout instruction is confirmed here, the controlling portion 31 returns to the processing of step S301 in FIG. 10 after executing predetermined logout processing, and repeats the subsequent processing.

On the other hand, if access from an internal terminal apparatus is not confirmed by the processing of step S331 described above, the controlling portion 31 proceeds to processing of step S341. At this point of time, it is already known that access from an external terminal apparatus has not been confirmed, by the processing of step S301 described above (FIG. 10).

Therefore, in this case, the file server 30 is in the waiting state of waiting for access from another apparatus.

At the same time, at step S341, the controlling portion 31 of the file server 30 executes processing for performing various kinds of analyses, for example, based on a plurality of pieces of image data accumulated in the image database 32 and a plurality of pieces of patient information recorded in the patient information database 34 and notifying a doctor's first terminal of results of the analyses as necessary.

More specifically, for example, analysis about progress of a disease condition based on change over time is performed in terms of a plurality of pieces of image data associated with particular patient information. Such analysis processing can be realized, for example, by utilizing AI and the like.

On the other hand, if access from an apparatus other than the second terminal 20 (that is, the first terminal 10) is confirmed by the processing of step S302 described above, and the controlling portion 31 proceeds to the processing of step S321, then the controlling portion 31 executes relevant information search processing at step S321. The relevant information search processing is processing for responding to an instruction given by a doctor to search for necessary information, for example, patient information such as an electronic medical record about a patient that the doctor is in charge of (in this case, a patient or the like who is a sender of request information) using the first terminal 10.

Then, at step S322, the controlling portion 31 makes photographic condition settings and the like for photographing of an image according to the request information. As for the processing performed here, the doctor may perform operation input using the first terminal 10 to specify various kinds of settings, or the controlling portion 31 (the order information creating portion 31b) of the file server 30 may automatically make the various kinds of settings.

Next, at step S323, the controlling portion 31 confirms whether or not an instruction to create general order information is given from the doctor's first terminal 10. If the general order information creation instruction from the doctor is confirmed, the controlling portion 31 proceeds to processing of next step S324. If the general order information creation instruction from the doctor is not confirmed, the controlling portion 31 judges that the doctor does not issue general order information according to the request information, returns to the processing of step S301 described above and enters the waiting state.

On the other hand, if the general order information creation instruction from the doctor is confirmed by the processing of step S323 described above, and the controlling portion 31 proceeds to the processing of step S324, then the controlling portion 31 confirms whether the doctor responds or not, at step S324. In this case, the response by the doctor refers to, for example, a case where, at the time of creating general order information corresponding to the request information using the first terminal 10, the doctor performs input for each item himself/herself.

If an instruction signal to the effect that the doctor responds himself/herself is confirmed, the controlling portion 31 proceeds to processing of next step S325, and the controlling portion 31 transmits the created general order information to the first terminal 10 at step S325. After that, the controlling portion 31 returns to the processing of step S301 described above and enters the waiting state.

On the other hand, if the instruction signal to the effect that the doctor responds himself/herself is not confirmed, the controlling portion 31 proceeds to processing of step S326, and the controlling portion 31 transmits the created general order information to the second terminal 20 at step S326. After that, the controlling portion 31 returns to the processing of step S301 described above and enters the waiting state.

If that request information is not received in the processing of step S303 described above is confirmed, and the controlling portion 31 proceeds to processing of step S311, then the controlling portion 31 confirms whether image data from the second terminal 20 has been received or not, at step S311. If reception of image data is confirmed, the controlling portion 31 confirms whether the image data satisfies predetermined conditions or not. The image data sent from the second terminal 20 is image data photographed according to the general order information. The predetermined conditions for the image data are conditions specifying that photographing should be performed according to the general order information, for example, conditions that a predetermined format should be adopted and that predetermined accompanying information should be attached.

If it is confirmed that image data has been received, and it is confirmed that the image data satisfies the predetermined conditions, the controlling portion 31 proceeds to processing of next step S312. If reception of image data is not confirmed or if, though reception of image data is confirmed, it is confirmed that the image data does not satisfy the predetermined conditions, the controlling portion 31 proceeds to processing of step S313.

At step S312, the controlling portion 31 records the image data to a predetermined area (for example, the image database 32) as a medical reference image and as patient information. At this time, the image data to be recorded and corresponding particular patient information are associated with each other. Then, a notification to the effect that a medical reference image corresponding to the general order information has been recorded is transmitted to the doctor's first terminal 10. After that, the controlling portion 31 returns to the processing of step S301 described above and enters the waiting state.

At step S313, the controlling portion 31 notifies the second terminal 20 that has transmitted the image data of a reason for the conditions not being satisfied, and the like. Here, the reason for the conditions not being satisfied is a reason why the received image data cannot be adopted as a medical reference data as a result of the confirmations in the processing of step S311 described above, that is, predetermined conditions that are not satisfied. After that, the controlling portion 31 returns to the processing of step S301 and enters the waiting state.

As described above, according to the one embodiment, the medical support system 1 for sharing patient information and supporting medical services is configured being provided with a first information terminal apparatus (the first terminal 10) having a communication function and an image pickup function and is configured to transmit particular use information (general order information) according to received request information, and a second information terminal apparatus (the second terminal 20) having at least a communication function and is configured to transmit inputted request information, and the medical support system 1 being configured so that the second information terminal apparatus records, at the time of recording acquired image data, the image data, associating the particular use information received from the first information terminal apparatus with the image data.

In the medical support system 1, when a non-medical worker such as a patient's family member transmits predetermined request information to the first information terminal apparatus (the first terminal 10) that a doctor has or the file server 30 using the second information terminal apparatus (the second terminal 20), the doctor performs, in response to the request information, a predetermined operation according to the received request information using the first information terminal apparatus (the first terminal 10). Consequently, particular use information (general order information) is created in the first information terminal apparatus (the first terminal 10) or the file server 30.

The particular use information (general order information) created in this way is transmitted to the second information terminal apparatus (the second terminal 20). In response to the particular use information, the non-medical worker such as a patient's family member performs photographing of an image using the second information terminal apparatus (the second terminal 20) to acquire image data of a target patient. Here, the second information terminal apparatus (the second terminal 20) records the acquired image data in association with the particular use information (general order information) received from the first information terminal apparatus (the first terminal 10) or the file server 30. Consequently, the acquired image data is in a state that can be approved as a medical reference image.

As described above, if information including an image photographing instruction and the like is included in general order information (a group of pieces of information equivalent to order information including a plurality of medical action instructions) as particular use information that is given by a doctor according to request information from a patient's family member, and photographing of an image is performed using the second terminal 20 which has received general order information, then various kinds of information included in the general order information are associated with acquired image data as medical metadata, and the image data is recorded.

The image data created in this way is shared as a reliable medical reference image by being transferred to the file server 30 or the like.

Therefore, if a patient's family member or the like at a remote location transmits predetermined request information to a doctor and receives particular use information (general order information), it is possible for the patient's family member to, only by photographing a target patient using the second terminal 20 which has received the particular use information (general order information), easily and certainly acquire a patient image according to the doctor's instruction (the general order information) without high-level photographing skills, predetermined photographing knowledge or the like, and acquire a medical reference image in a form of image data to which medical metadata is attached.

The medical support system 1 of the present embodiment enables not only image information as patient information acquired by a medical worker but also image information acquired by a general person (a non-medical worker) other than medical workers to be handled as a medical image or medical reference image as patient information, and makes it possible to enhance convenience of medical actions.

In this case, since it is possible to create an image data file in a form of medical basic information and the like included in general order information being associated with image data as medical metadata even at the time of photographing an image, it is possible to prevent mistaken selection of image data and the like, and it is also possible to improve reliability of information. Further, it becomes easy to manage valuable image information.

Since the second information terminal apparatus (the second terminal 20) is adapted to create an image data file in a form of medical basic information and the like included in general order information being associated with acquired image data as medical metadata (accompanying information), it is possible to, for example, even if the image data is transferred to another device, easily identify which kind of image data the image data is only by referring to the accompanying information. For example, since a unique number (referred to as an order number or the like) included in general order information is associated with a patient ID, an examination ID and the like, the unique number facilitates identification of a patient, and association with a series of examination studies and particular affection/disease examinations becomes possible.

Note that though description has been made with a general portable image pickup apparatus (camera), a smartphone, a tablet PC or the like provided with an image pickup function and a communication function as an example of one form of the information terminal apparatus (10, 20) in the one embodiment describe above, the form of an information terminal apparatus applicable to the present invention is not limited to the above forms.

For example, in recent years, a camera system has been in practical use and widespread in which it is enabled to always watch over (monitor) a situation of a target patient to be photographed from a remote location, by installing a camera at a predetermined place (for example, the target patient's home or a hospital room in a hospital), remotely operating the camera via a network to acquire photographed images at predetermined time intervals, and transferring the acquired photographed images to another apparatus (such as a file server) via the network (a network camera system called a so-called watching (surveillance) camera, a web camera or the like).

A camera included in this type of network camera system can be applied as the information terminal apparatus of the present invention.

Though a system used in the medical field is illustrated in the one embodiment described above, the present invention is not limited to the example but can be easily applied to fields other than the medical field, for example, a video field and a scientific research field.

That is, it is possible to construct a system capable of associating accompanying information including particular use information created by a specialist in each of various kinds of fields with image data acquired by an ordinary person through a predetermined procedure, similarly to the one embodiment described above. The information for particular use may be expressed as including photographing condition information and information clarifying being used for a medical action.

Thus, according to the present invention, a non-medical worker can easily obtain reliable image information to be an aid to medical care and diagnosis for a doctor at a remote place, using a general terminal such as a camera or a smartphone.

In that case, by recording image data obtained by attaching accompanying information including particular use information created by specialists to a predetermined file sever to obtain a database, it is possible to secure reliability of each piece of image data, and contribute to improvement of reliability of an image database in each field.

Note that, as for each processing sequence described in the one embodiment described above, change in a procedure can be permitted unless contrary to the nature of the processing sequence. Therefore, for each processing sequence, it is possible, for example, to change execution order of respective processing steps, cause a plurality of processing steps to be executed at the same time, cause the order of the respective steps to be different each time a series of processing sequences is executed. That is, even if description is made on an operation flow in Claims, the specification and the drawings using "first", "next" and the like for convenience, it is not meant that it is indispensable to implement the operation flow in that order. It goes without saying that, at each of steps constituting each operation flow, a part that does not influence the essence of the invention can be appropriately omitted.

Among the techniques described here, many of the controls and functions mainly described using a flowchart can be often set by a software program, and the above controls and functions can be realized by a computer reading and executing the software program. The software program is electronic data the whole or part of which is recorded in a recording medium, a storage portion or the like, more specifically, for example, a portable medium such as a flexible disk, a CD-ROM and a non-volatile memory or a storage medium such as a hard disk and a volatile memory during a product manufacturing process in advance as a computer program product. Aside from the above, the software program can be distributed or provided at product shipment, or can be distributed or provided via portable media or communication lines. Even after product shipment, a user can cause the program software to operate by downloading the software program via a communication network or the Internet himself/herself and installing the software program into a computer, or by installing the program software into the computer from a storage medium, and it is thereby possible to easily realize the medical support system and the information terminal apparatus of the present embodiment.

It is also possible to appropriately replace a part configured with a program with a circuit. Note that each part expressed as "portion" (a section or a unit) in the embodiment may be configured with a dedicated circuit or a combination of a plurality of general-purpose circuits. If necessary, the part may be configured with a processor such as a microcomputer or a CPU that operates according to software programmed in advance, or a combination of sequencers such as FPGAs. Such design is also possible that a part or all of control of the part is undertaken by an external apparatus. In this case, a wired or wireless communication circuit is interposed. Communication can be performed via Bluetooth, WiFi, a telephone line or the like, and can be also performed via USB. Dedicated circuits, general-purpose circuits and controlling portions may be integrally configured as an ASIC. A part that is mechanically position-controlled is configured with various actuators and, if necessary, a coupling mechanism for movement, and the actuators are operated by drive circuits. The drive circuits are also controlled by a microcomputer or an ASIC according to a particular program. Such control may be corrected or adjusted in detail by information outputted by various sensors or peripheral circuits of the various sensors.

The present invention is not limited to the one embodiment described above, and it is, of course, possible to make various modifications and applications within a range not departing from the spirit of the invention. Furthermore, the above one embodiment includes inventions at various stages, and various inventions can be extracted by an appropriate combination among a plurality of disclosed constituent features. For example, even if some constituent features are deleted from all the constituent features shown in the above one embodiment, a configuration obtained after deleting the constituent features can be extracted as an invention if the problem to be solved by the invention can be solved, and the advantageous effects of the invention can be obtained. Furthermore, components of different embodiments may be appropriately combined. The present invention is limited only by accompanying claims and not restricted by a particular practiced aspect of the present invention.

What is claimed is:

1. A medical support system supporting medical services even at a remote location, the medical support system comprising:
    a first information terminal apparatus for operation by a doctor, including (1) an input, (2) a display, and (3) a communication portion,
    wherein the communication portion is configured to receive, from a remotely located second information terminal apparatus, request information, the request information including both patient identification information and additional information,
    wherein, responsive to receiving the request information, the input is configured to receive doctor input, and
    wherein the communication portion is configured to transmit, to the remotely located second information terminal apparatus, general order information derived from or including the doctor input, the general order information including photographing condition information for a helper to photograph a patient using the second information terminal apparatus; and
    the second information terminal apparatus for operation by the helper, including (1) an image pickup portion, (2) a display, and (3) a communication portion,
    wherein, the communication portion of the second information terminal apparatus (1) transmits the request information to the first information terminal apparatus, and (2) receives the general order information,
    wherein the display displays guidance information included in or derived from the photographing condition information received from the first information terminal apparatus to assist the helper to photograph the patient,
    wherein the image pickup portion captures at least one image of the patient responsive to helper input,
    wherein the general order information includes information provided by the doctor via the first information terminal apparatus, and
    wherein the information provided by the doctor is checked to determine whether or not it is too difficult to execute by the helper, and responsive to a determination that the information is too difficult to execute by the helper, the information is changed to simplified information included in the general order information.

2. The medical support system according to claim 1, wherein the second information terminal apparatus further includes a confirmation circuit for confirming the patient before photographing the patient.

3. The medical support system according to claim 1, wherein, at a time of recording information acquired by an image pickup function, the second information terminal apparatus records the information, associating the photographing condition information received from the first information terminal apparatus with the information.

4. The medical support system according to claim 1, wherein, besides the photographing condition information according to the request information from the helper, the first information terminal apparatus transmits information clarifying that the photographed image is for a medical action performed for the patient.

5. The medical support system according to claim 4, wherein the second information terminal apparatus further transmits particular use image data with which particular use information including the photographing condition information and the information clarifying being used for a medical action is associated.

6. The medical support system of claim 1 wherein the image pickup portion is part of a general image apparatus, but wherein the at least one image of the patient is saved as a medical reference image.

7. The medical support system of claim 1 wherein the general order information includes information for automatically setting parameters of the image pickup portion.

8. The medical support system of claim 1 wherein the additional information included in the request information includes recent situation information about the patient.

9. The medical support system of claim 1 wherein the communication portion of the second information terminal apparatus transmits the at least one image of the patient to at least one of the first information terminal apparatus and a file server.

10. The medical support system of claim 1, wherein the helper is the patient.

11. An information terminal apparatus comprising:
    a communication device comprising
    a transmitting device configured to transmit request information from a photographer to a remotely located other information terminal apparatus, the request information including both patient identification information and additional information, and
    a receiving device configured to receive, after the transmitting device has transmitted the request information, particular use information from the remotely located other information terminal apparatus, the particular use information including photographing condition information created based on the request information and information clarifying being used for a medical action;
    an image pickup device configured to acquire image data;
    a processor configured to associate the image data acquired by the image pickup device with the particular use information received by the communication device; and
    a recording device configured to record particular use image data in a form in which the image data and the particular use information are associated by the processor,
    wherein the general order information includes information provided by the doctor via the first information terminal apparatus, and wherein the information provided by the doctor is checked to determine whether or not it is too difficult to execute by the helper, and responsive to a determination that the information is too difficult to execute by the helper, the information is changed to simplified information included in the general order information.

12. The information terminal apparatus according to claim 11, wherein the request information includes information about a target patient and a user that uses the information terminal apparatus.

13. The information terminal apparatus according to claim 11, wherein the request information includes information about apparatuses usable by the user that uses the information terminal apparatus.

14. The information terminal apparatus according to claim 11, wherein the request information includes skills information about the user that uses the information terminal apparatus.

15. The information terminal apparatus according to claim 11, wherein the communication portion transmits the particular use image data.

16. The information terminal apparatus according to claim 11, further comprising:
a display portion configured to display an image based on the image data and various kinds of setting information; and
an image pickup controlling portion configured to perform image pickup control of the image pickup portion and display control of the display portion; wherein
at a time of photographing an image according to the particular use information, the image pickup controlling portion displays the image data obtained by the image pickup portion on the display portion and displays guidance information included in the particular use information on the display portion.

17. The information terminal apparatus according to claim 16, wherein the guidance information includes guidance information changed according to the request information.

18. The information terminal apparatus of claim 11 wherein the helper is the patient.

19. A method for acquiring patient image data with a medical support system including a first information terminal apparatus for use by a doctor and a second information terminal apparatus, remote from the first information terminal apparatus, for use by a helper, the method comprising:
receiving as input, by the second information terminal apparatus, request information including both patient identification information and additional information;
transmitting, from the second information terminal apparatus to the first terminal, the request information;
receiving, by the second information terminal apparatus, the request information;
responsive to receiving the request information, receiving doctor input;
creating, general order information derived from or including the doctor input, the general order information including photographing condition information for the helper to photograph a patient using the second information terminal apparatus;
displaying, on a display of the second information terminal apparatus terminal, guidance information included in or derived from the photographing condition information received from the first information terminal apparatus to assist the helper to photograph the patient; and
capturing, with an image pickup portion of the second information terminal apparatus, at least one image of the patient responsive to helper input,
wherein the general order information includes information provided by the doctor via the first information terminal apparatus, and
wherein the information provided by the doctor is checked to determine whether or not it is too difficult to execute by the helper, and responsive to a determination that the information is too difficult to execute by the helper, the information is changed to simplified information included in the general order information.

20. The patient image data acquisition method according to claim 19, wherein the particular use information includes guidance information changed according to the request information.

21. The patient image data acquisition method according to claim 19, wherein the request information includes information about the patient.

22. The patient image data acquisition method according to claim 19, further comprising performing identification of the patient according to the particular use information.

23. The method of claim 19, further comprising:
transmitting the at least one image of the patient to at least one of the first information terminal apparatus and a file server.

24. The method of claim 19, wherein the helper is the patient.

25. The method of claim 19, wherein the helper is the patient.

26. A method for acquiring patient image data with a medical support system including a first information terminal apparatus for use by a doctor and a second information terminal apparatus, remote from the first information terminal apparatus, for use by a helper, the method comprising:
receiving as input, by the second terminal, request information including both target patient identification information and additional information;
transmitting, from the second information terminal apparatus to the first information terminal apparatus, the request information;
receiving, by the second information terminal apparatus, the request information;
responsive to receiving the request information, receiving doctor input;
creating, general order information derived from or including the doctor input;
capturing, with an image pickup portion of the second information terminal apparatus, at least one image of the patient responsive to helper input; and
recording the image in association with the doctor input information,
wherein the general order information includes information provided by the doctor via the first information terminal apparatus, and
wherein the information provided by the doctor is checked to determine whether or not it is too difficult to execute by the helper, and responsive to a determination that the information is too difficult to execute by the helper, the information is changed to simplified information included in the general order information.

* * * * *